(12) United States Patent
Tornblom

(10) Patent No.: US 10,357,604 B2
(45) Date of Patent: *Jul. 23, 2019

(54) VALVE AND A METHOD FOR ADMINISTERING A PLURALITY OF DRUG FLUIDS

(71) Applicant: CYTO365 AB, Viken (SE)

(72) Inventor: Micael Tornblom, Viken (SE)

(73) Assignee: CYTO365 AB, Viken (SE)

( * ) Notice: Subject to any disclaimer, the term of this patent is extended or adjusted under 35 U.S.C. 154(b) by 324 days.

This patent is subject to a terminal disclaimer.

(21) Appl. No.: 15/064,422

(22) Filed: Mar. 8, 2016

(65) Prior Publication Data

US 2017/0258991 A1 Sep. 14, 2017

(51) Int. Cl.
| | |
|---|---|
| *A61M 5/14* | (2006.01) |
| *A61M 39/22* | (2006.01) |
| *A61M 5/168* | (2006.01) |
| *A61M 39/24* | (2006.01) |
| *F16K 11/085* | (2006.01) |

(52) U.S. Cl.
CPC ...... *A61M 5/16827* (2013.01); *A61M 5/1407* (2013.01); *A61M 5/1409* (2013.01); *A61M 5/16881* (2013.01); *A61M 39/223* (2013.01); *A61M 39/225* (2013.01); *A61M 39/24* (2013.01); *F16K 11/085* (2013.01); *A61M 2005/1402* (2013.01); *A61M 2005/1403* (2013.01); *A61M 2039/229* (2013.01)

(58) Field of Classification Search
CPC .......... A61M 5/16827; A61M 5/16881; A61M 5/1407; A61M 5/1409; A61M 2005/1402; A61M 2005/1403; A61M 39/223; A61M 39/225; A61M 39/24
See application file for complete search history.

(56) References Cited

U.S. PATENT DOCUMENTS

| | | |
|---|---|---|
| 2,485,842 A | 10/1949 | Pennington |
| 3,618,637 A | 11/1971 | Santomieri |
| 3,834,372 A | 9/1974 | Turney |
| 3,957,082 A | 5/1976 | Fuson et al. |
| 4,219,021 A | 8/1980 | Fink |
| 4,604,093 A | 8/1986 | Brown et al. |
| 4,608,996 A | 9/1986 | Brown |
| 4,758,235 A | 7/1988 | Tu |

(Continued)

FOREIGN PATENT DOCUMENTS

| | | |
|---|---|---|
| WO | 9118632 A1 | 12/1991 |
| WO | 2006025054 A2 | 3/2006 |

(Continued)

*Primary Examiner* — Rebecca E Eisenberg
*Assistant Examiner* — Tasnim Mehjabin Ahmed
(74) *Attorney, Agent, or Firm* — David J. Pitman; Fulwider Patton LLP

(57) ABSTRACT

A valve and a method for administering a plurality of drug fluids to a patient are disclosed. For each drug fluid, the valve may be rotated into a selected drug position associated with the drug fluid. With the valve being in the selected drug position, a backpriming may be performed of a connector line of a drug container containing the drug fluid. Thereafter, the drug fluid may be administered with the valve being in the same selected drug position. Thereafter, the valve may be flushed, optionally while maintaining the same selected valve position.

17 Claims, 20 Drawing Sheets

(56) References Cited

U.S. PATENT DOCUMENTS

| | | | |
|---|---|---|---|
| 4,900,322 A | | 2/1990 | Adams |
| 4,967,797 A | | 11/1990 | Manska |
| 5,097,840 A | | 3/1992 | Wallace et al. |
| 5,104,387 A | * | 4/1992 | Pokorney ............ A61M 39/223 137/625.47 |
| 5,135,026 A | | 8/1992 | Manska |
| 5,288,290 A | | 2/1994 | Brody |
| 5,439,452 A | | 8/1995 | McCarty |
| 5,647,845 A | | 7/1997 | Haber et al. |
| 7,695,445 B2 | | 4/2010 | Yuki |
| 7,984,730 B2 | | 7/2011 | Ziv et al. |
| 2003/0125673 A1 | * | 7/2003 | Houde ................ A61M 39/223 604/246 |
| 2006/0089603 A1 | | 4/2006 | Truitt et al. |
| 2010/0305507 A1 | | 12/2010 | Duncan |
| 2011/0071390 A1 | | 3/2011 | Liu et al. |
| 2014/0224829 A1 | | 8/2014 | Capone et al. |
| 2014/0346386 A1 | * | 11/2014 | Tornblom ........... A61M 39/223 137/625.19 |

FOREIGN PATENT DOCUMENTS

| | | |
|---|---|---|
| WO | 2011011057 A2 | 1/2011 |
| WO | 2013055278 A1 | 4/2013 |
| WO | 2013146752 A1 | 10/2013 |

\* cited by examiner

SECTION A-A

SECTION A-A

SECTION B-B

SECTION C-C

SECTION D-D

SECTION A-A

SECTION B-B

SECTION C-C

SECTION D-D

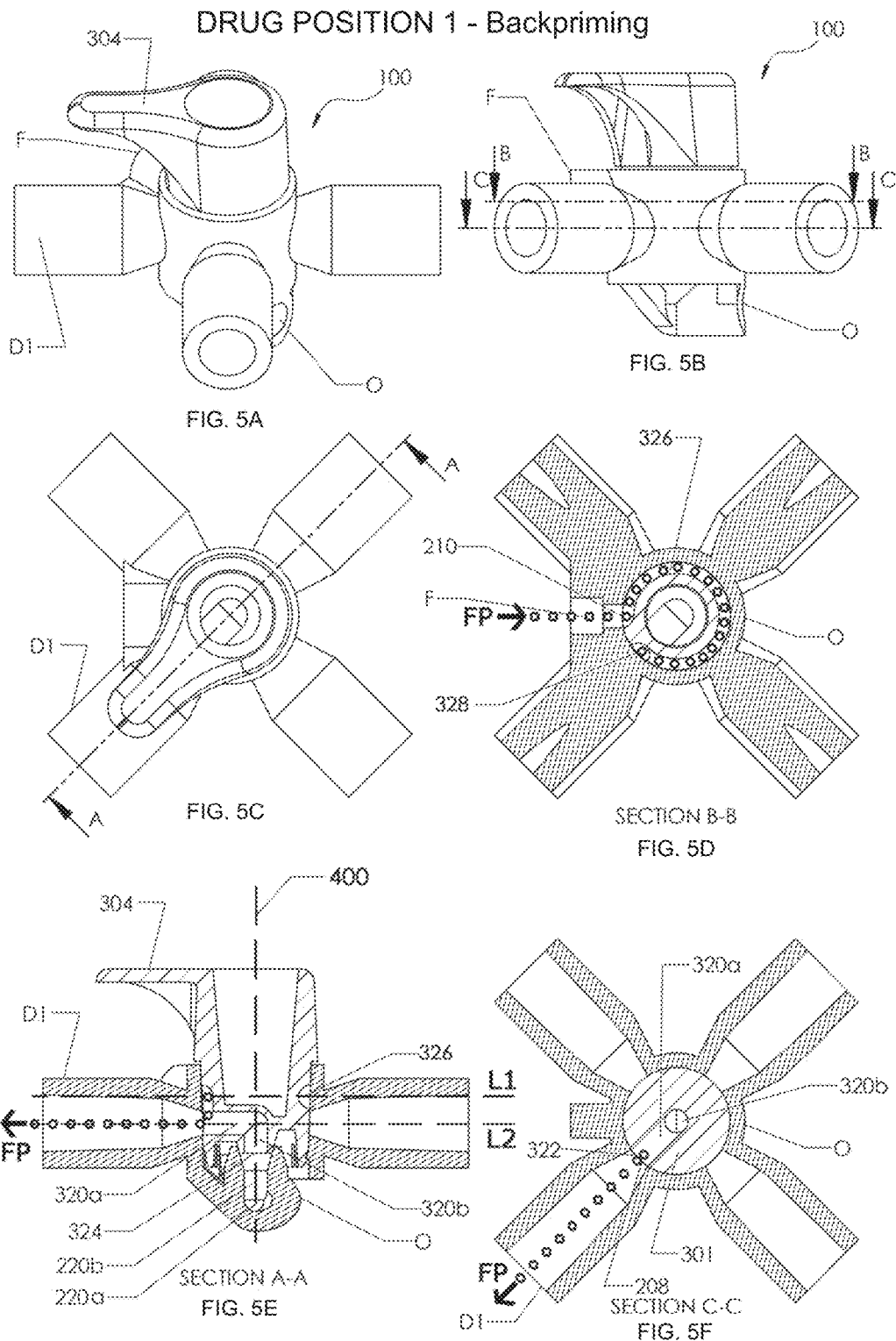

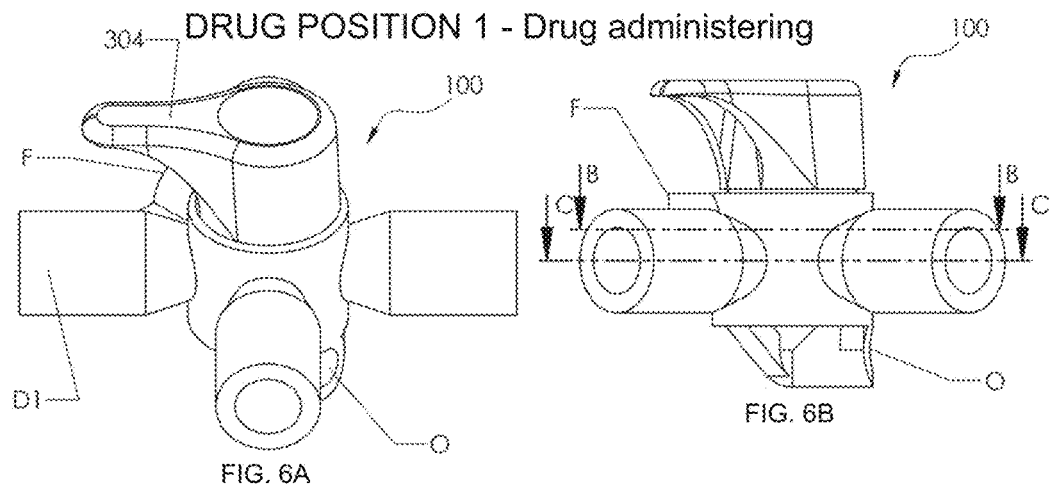
FIG. 6A
FIG. 6B
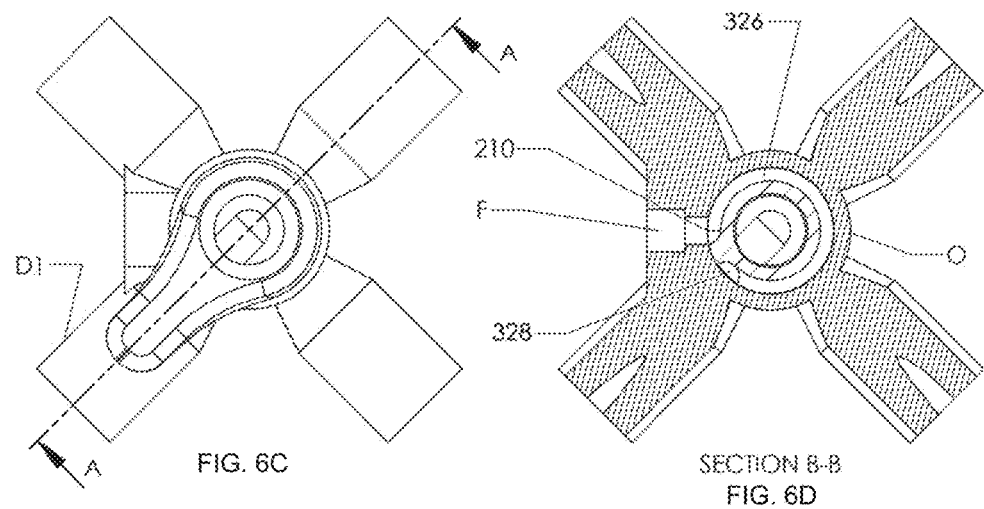
FIG. 6C
SECTION B-B
FIG. 6D
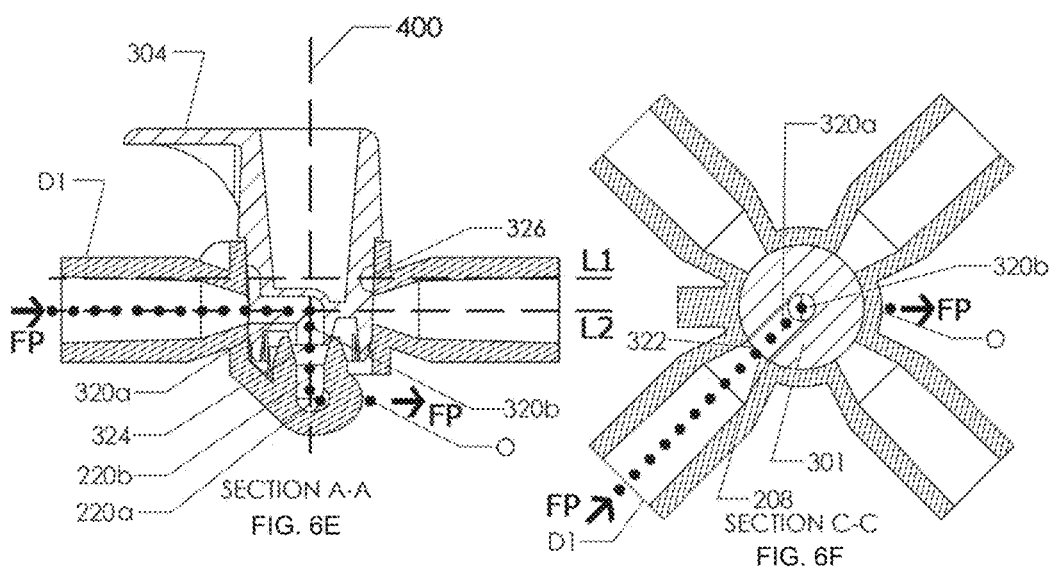
SECTION A-A
FIG. 6E
SECTION C-C
FIG. 6F

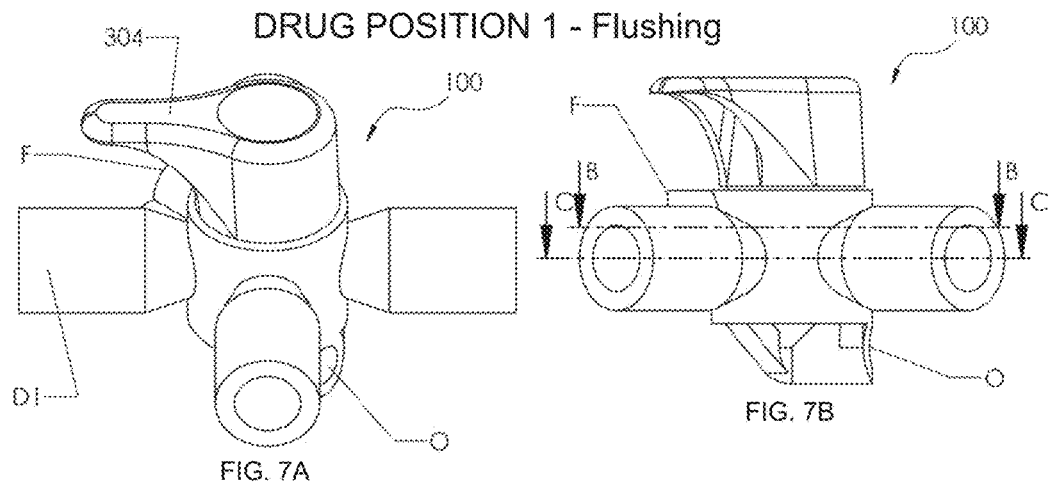
FIG. 7A  FIG. 7B
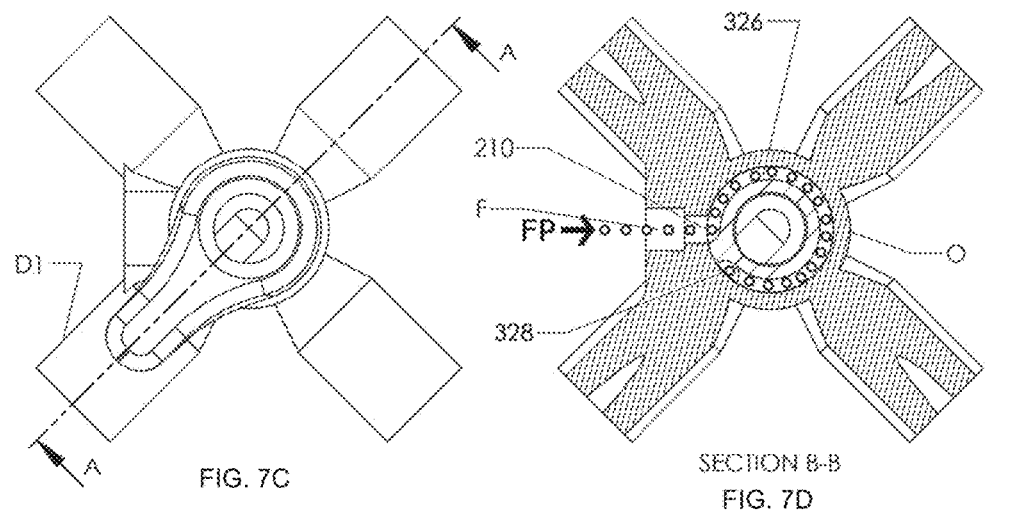
FIG. 7C  SECTION B-B FIG. 7D
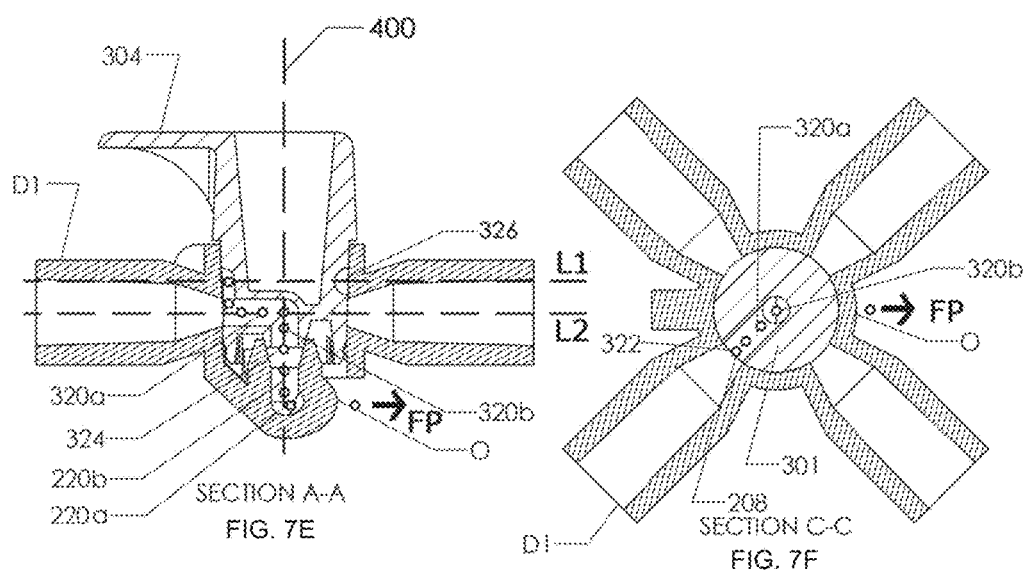
SECTION A-A FIG. 7E  SECTION C-C FIG. 7F

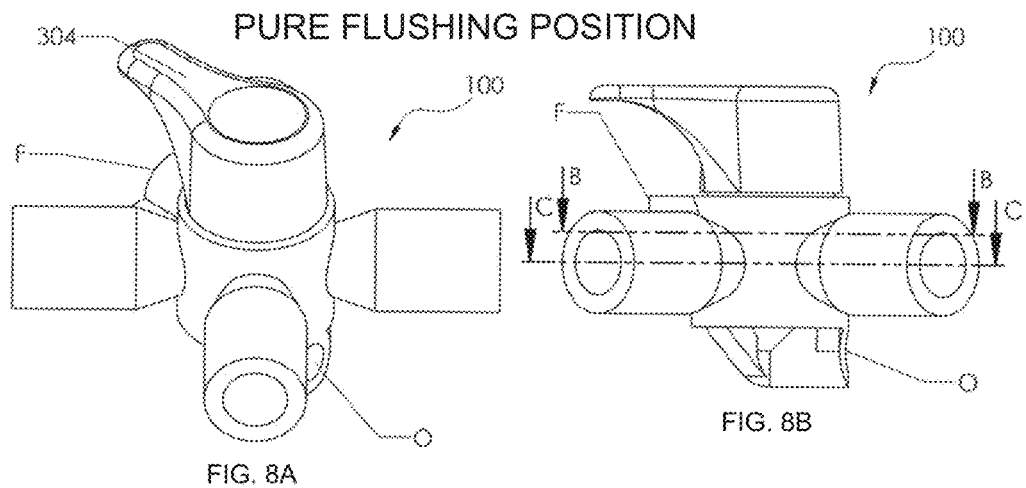
FIG. 8A
FIG. 8B
PURE FLUSHING POSITION
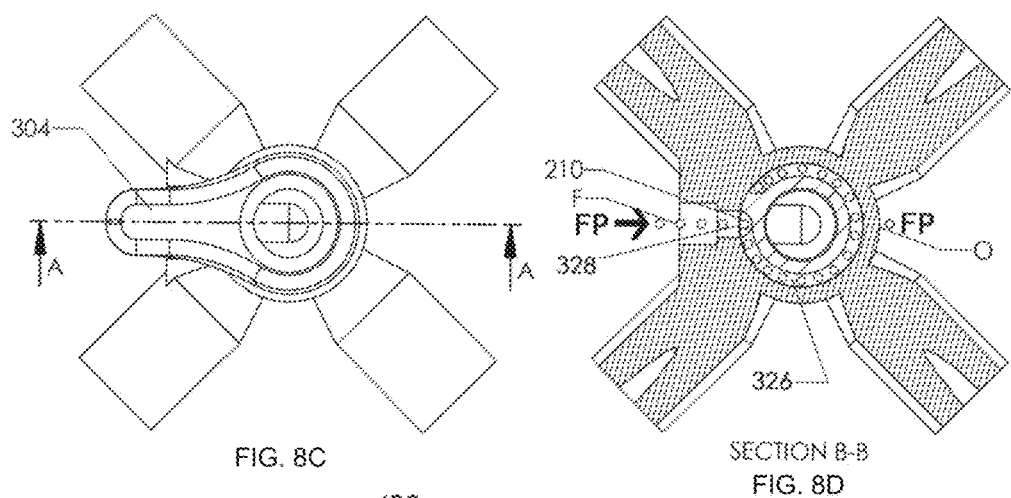
FIG. 8C
SECTION B-B
FIG. 8D
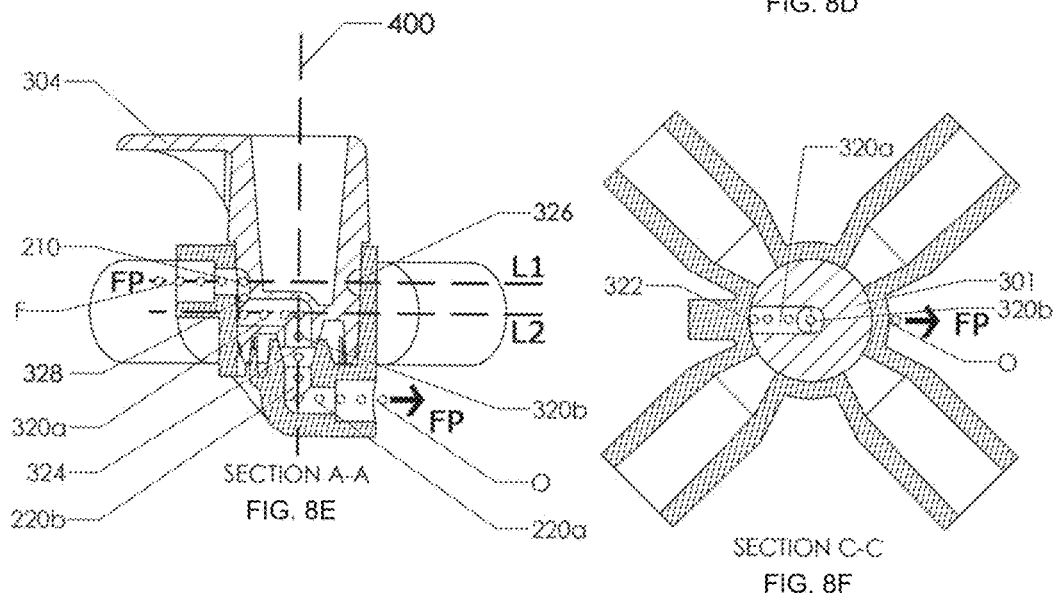
SECTION A-A
FIG. 8E
SECTION C-C
FIG. 8F Backpriming D1

Backpriming D2

Administering D1

Administering D2

Flushing D1

Flushing D2

SECTION A-A

SECTION A-A

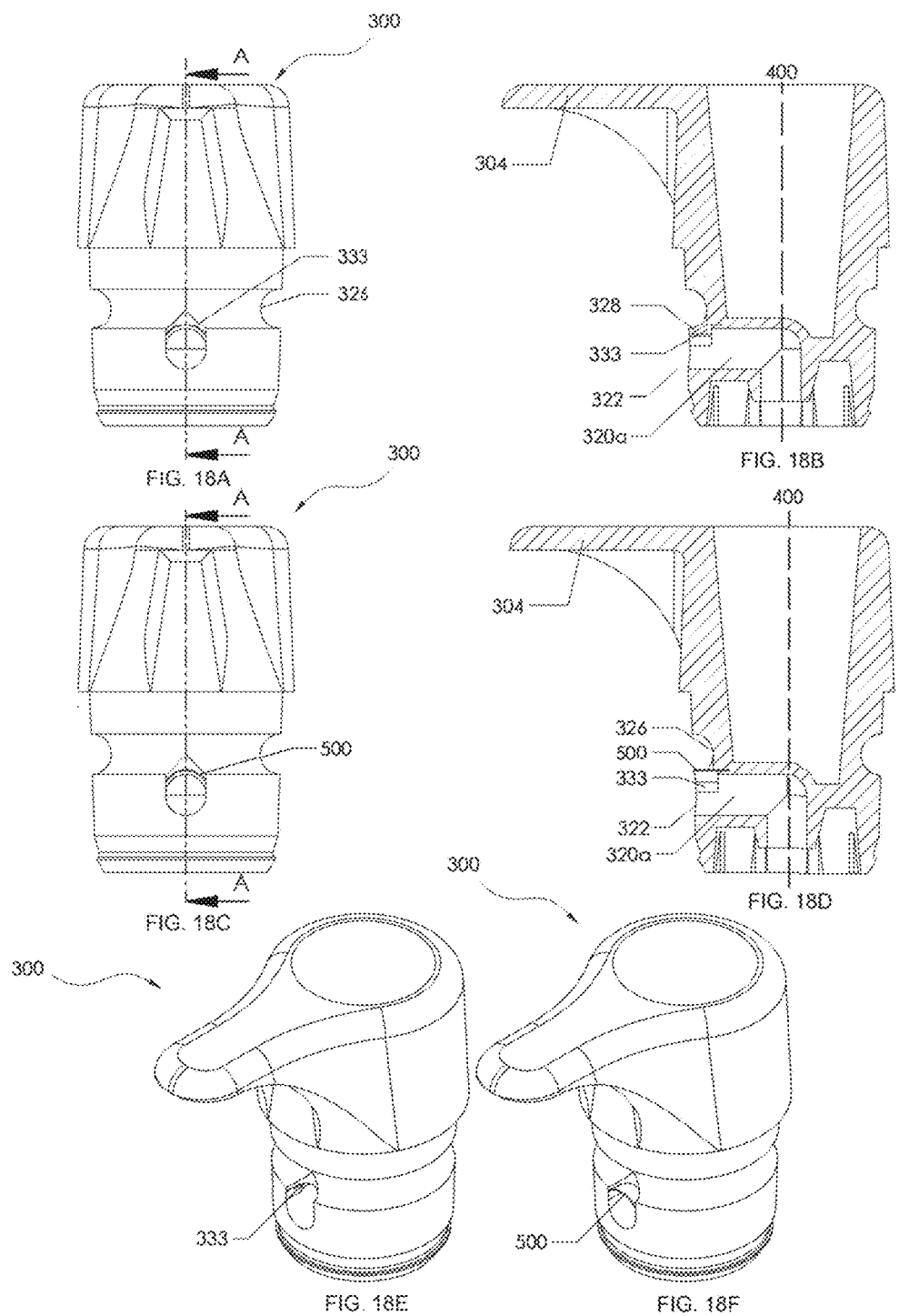

VALVE AND A METHOD FOR ADMINISTERING A PLURALITY OF DRUG FLUIDS

TECHNICAL FIELD

The present invention relates to administration of drug fluids. More specifically, the invention relates to a valve and a method for sequential administration of a plurality of drug fluids to a patient, such as cytostatics, antibiotics, nutritions and electrolytes.

BACKGROUND

Present Multi-drug Intravenous Therapy Systems

FIG. 12 schematically illustrates an intravenous (IV) therapy system 10 typically used in the U.S. and FIG. 13 schematically illustrates an IV therapy system 10' typically used in Europe. Where appropriate, the same reference numerals are used in FIGS. 12 and 13 to designate similar components.

Both IV systems 10 and 10' are designed for administering a neutral fluid A, such as a saline fluid, and two or more different drug fluids B and C to a patient. Each system 10, 10' comprises three interconnected IV infusion sets, each IV infusion set including at least a pre-filled, sterile container, a sterile connector tube or line, a clamp or a valve to regulate or stop the flow, and a connector, such as a Luer connector, at the end of the connector line.

In the field of IV infusion where both a neutral fluid, such as a saline fluid, and one or more drug fluids are to be administered to a patient, the terminology normally used in the art is that the infusion of the neutral fluid is referred to as the "primary infusion" or "main line", whereas the infusion of a drug fluid is referred to as the "secondary infusion" or "secondary line". This terminology will be used in the present application. However, for the sake of clarity and explanation in the present application, where appropriate the more descriptive terms "saline" or "flushing" and "drug" will be used as equivalents to "primary" and "secondary", respectively. The term "downstream" refers to a direction towards the patient, whereas the term "upstream" refers to a direction opposite to downstream.

An IV infusion set may also include a drip chamber which captures any air bubbles occurring in the IV infusion set.

Using the above terminology, the U.S. system 10 in FIG. 12 comprises a primary or main IV set 16, a first drug IV set 16B and a second drug IV set 16C. The main IV set 16 includes a saline container 12A containing a neutral fluid A, such as saline, a drip chamber 14A normally located adjacent the saline container 12A on the main IV line upper part 16A and a saline back check valve 17A on the main IV line upper part 16A. The first and second drug IV sets 16B and 16C include first and second drug containers 12B and 12C, respectively, first and second drug drip chambers 14B and 14C, respectively, and first and second drug clamps that normally is either a slide clamp, pinch clamp or rollerclamp, 18B and 18C, respectively. The first and second drug IV sets are connected to the main IV line 16 via Y-ports 20B and 20C, respectively. The main IV line 16 is connected to the patient, optionally via an infusion pump 30 to control the infusion flow rate, or via gravity only where the infusion rate is controlled by e.g. a roller clamp 18A.

The European infusion system 10' in FIG. 13 presents at least the following differences in relation to the U.S. system 10 in FIG. 12:

In the European system 10', the first and the second drug IV sets have no drip chamber of their own but are instead connected to the main IV line 16 upstream (above) the main drip chamber 14A, which thereby operates as a common drip chamber for the whole system 10'.

In the European system 10', each one of the first and the second drug IV sets 16B, 16C also includes a back check valve 17B and 17C, respectively.

In the European system 10', the upper part 16A of the main IV line 16 includes a clamp 18A used to open and close the flow from the saline container 12A.

The U.S. system 10, when administering e.g. the first drug B, has an open flow line on both the primary line 16A, and secondary line 16B, and therefore relies on hydrostatic pressure difference between the primary and secondary infusion containers to obtain the infusion sequence, where the secondary infusion gets infused first due to higher pressure, while stopping the primary infusion with back pressure. After the secondary infusion has run empty, the back pressure on the primary infusion releases and allows the primary infusion to run. In contrast, in the European system all infusion containers normally hanging on about the same level with no or very little hydrostatic pressure difference, and the primary infusion needs to be closed with a clamp 18A while the secondary infusion runs.

When using the systems 10 and 10', priming of the main IV line 16A is normally done by squeezing the main drip chamber 14A to fill it about halfway, and then opening the clamp or clamps on the main line to let he saline flow though the main IV line 16A out through the initially free end of the tubing. Since this main IV line 16A normally contains neutral saline this method may be considered to be safe. Once the main IV line 16A has been primed, it may be connected to the patient with a connector that may be of Luer type In U.S. system 10, a drug IV set is delivered with the drug line being initially empty. Before connecting a secondary line to the main IV line 16, the secondary line should be primed to avoid air bubbles in the system. There are mainly two different methods used: priming the secondary line before the secondary fluid or drug fluid is connected to the main line, or backpriming the secondary line after it has been connected to the main IV line.

The first method, priming out of the free end, is performed as follows: the drug lines 16B and 16C may be primed in the same manner as with the main IV line 16A, which would involve letting the drug fluid flow downstream from the drug container B, C, and out from the free tubing end before the drug line is connected to the main IV line 16. However, when the secondary fluid is a drug, this method may be considered to be less safe.

The second method, backpriming, is performed as follows and is possibly the safest method of the two: the user connects one end of the initially empty secondary line 16B, 16C to the drug container 12B, 12C by spiking the drug container and holding the latter upside down in order to avoid spillage. Once connected, the other (downstream) end of the drug line is connected to the main IV line 16. Thereafter, a so-called backpriming of the drug line is performed. The backpriming of the drug line is achieved by holding the drug container at a level with lower hydrostatic pressure than the saline container 12A, then opening the clamp 18B, 18C on the drug line and then letting the saline fluid backprime (fill) the drug line. Since the drug line in the U.S. system 10 normally has a drip chamber 14B, 14C, this drip chamber will now start to fill up and the filling thereof should be stopped when it is half full by closing the clamp 18B, 18C or by holding the drug container at a higher level than the saline container.

In contrast to the U.S. system, in the European system 10' in FIG. 13 a drug IV set is normally delivered from the pharmacy with the drug line (16B, 16C) being pre-primed with saline and with a clamp (18B, 18C) fitted to the drug line. The drug line is usually not filled all up to the very end, so this may require a priming sequence similar to the U.S. system allowing fluid escape out of the free end, but this is safer than the first method explained in the U.S system since a possible first spillage would be the prefilled saline. Since connecting the secondary line, even if it is pre-primed, may involve a risk of an air bubble being trapped when the line is connected to the main IV line 16A, the main drip chamber 14A in this system 10' is arranged downstream the Y ports 20B, 20C in order to capture any potential air bubble.

When performing an infusion using the systems 10 and 10' described above, the normal infusion sequence would be as follows:

To verify that the system is set up correctly, the primary or saline fluid flow is first opened by opening the clamp on the main IV line 16. Then the nurse may verify that the fluid flows by noticing that there is dripping in the drip chamber and there is no bulge formed on the patient at the infusion site and no leakage, and by verifying that the IV set functions properly and is correctly connected to the patient's vein or other checks governed by local protocols. The basic, first function of the first saline is to prepare the patient for receiving infusion and to verify that the infusion functions properly.

Next, a first drug fluid will be administered and the associated drug container is normally emptied before the saline is again opened to flush the main IV line from drug residuals and to dilute the previous drug fluid into the vascular system of the patient. Thereafter, a subsequent, second drug fluid will be administered.

Finally, after all drug fluids have been administered, the saline is again used to dilute the drug into the patient's vascular system before ending the treatment.

Infusion pumps may be used to have a better control over the infusion flow rates instead of verifying the infusion flow rate by counting the drip rate in the drip chamber. An infusion pump may also be used for other safety purposes, such as generating an alarm if an air bubble occurs in the system or if the system runs empty.

There are plenty of medical situations in which a multiple of drug fluids to be administered into a patient has to be handled. In chemotherapy it is often of utmost importance to handle drug fluids to a patient which is treated for cancer in a reliable and safe manner. However, due to stressful working environments, tiredness, the human factor, etc., the handling of these drug fluids, including their connections, dosages, priming of infusion lines, etc. may lead to errors. For example, there is a need to clearly separate different fluids from each other, since they may chemically react in an undesired manner.

Applicant's WO 2013/055278 discloses a multiple-drug valve for administration of a plurality of drug fluids, such as cytostatics. This prior-art multiple-drug valve comprises a housing having a plurality of circumferentially distributed primary inlets for receiving a respective one of the drug fluids and a secondary inlet for receiving a secondary fluid, such as a neutral fluid. The valve has an outlet from which the fluids will be directed to the patient. A rotary valve member is arranged in the housing. The housing has a plurality of primary valve positions in each of which an associated one of the primary inlets is connected to the outlet, and a plurality of intermediary valve positions in each of which the secondary inlet is connected to the outlet. Moreover, the valve member has an outer surface sealingly engaging an inner surface of the housing, such that the primary and secondary inlets are sealingly connected to openings arranged in the outer surface of the valve member in each of the primary and intermediary valve positions, respectively.

Parallel infusion of incompatible drugs is generally not allowed, nor temporary mixing of incompatible drug fluids due to drug fluid residuals in the rotatable valve member.

SUMMARY OF THE INVENTION

An object of the invention is to provide a valve and a method for use in performing a sequential administering of a plurality of drug fluids.

The inventive valve makes it possible to perform backpriming of non-primed drug lines, each of which is connected to an associated container containing a respective one of the drug fluids to be administered, said backpriming being performed before the drug fluids are administered to a patient via the valve.

The inventive valve makes it possible to perform a complete flushing of the valve after administering a drug fluid and before administering another drug fluid, thereby eliminating or at least substantially reducing the risk of drug incompatibility within the valve.

The inventive valve makes it possible to perform, for each one of a plurality of drug fluids, a backpriming, a drug administering and a flushing by using the same valve for all the drug fluids and by using one and the same selected valve rotational position for each one of the drug fluids, and all this with a high degree of security when shifting from one drug fluid to a subsequent drug fluid, eliminating or at least substantially reducing the risk of drug incompatibility within the valve.

According to the inventive concept, there is provided a valve for administering two or more drug fluids, comprising:
   a rotational axis,
   a housing having:
   an inner cavity
   an inner circumferential surface,
   one flushing inlet for receiving a flushing fluid, the flushing inlet being fluidly connected to a flushing outlet, which opens into the inner cavity and is positioned on a first level with respect to the rotational axis, and
   a plurality of drug inlets, each drug inlet for receiving an associated drug fluid and each drug inlet being fluidly connected to an associated drug outlet opening into the inner cavity and being positioned on a second level that is different from the first level; and
   a valve member having:
   an outer circumferential surface, and
   a main passageway presenting an inlet arranged in the outer circumferential surface at the second level and an outlet arranged coaxially with the rotational axis;
   wherein the valve member is arranged to be rotated into any selected one of a plurality of drug positions, each drug position being associated with a respective one of said drug outlets; and
   wherein, in each selected drug position, the drug outlet which is associated with the selected drug position is fluidly connected to both the inlet of the main passageway and to the flushing outlet.

According to the inventive concept, there is also provided a valve for administering two or more drug fluids comprising:
- an outlet,
- a rotational axis,
- a housing having:
- an inner cavity
- an inner circumferential surface,
- one flushing inlet for receiving a flushing fluid, the flushing inlet being fluidly connected to a flushing outlet, which opens into the inner cavity and is positioned on a first level with respect to the rotational axis, and
- a plurality of drug inlets, each drug inlet for receiving an associated drug fluid and each drug inlet being fluidly connected to an associated drug outlet opening into the inner cavity and being positioned on a second level that is different from the first level; and
- a valve member having:
- an outer circumferential surface, and
- a main passageway presenting an inlet arranged in the outer circumferential surface at the second level and an outlet arranged coaxially with the rotational axis;
- wherein the valve member is arranged to be rotated into any selected one of a plurality of positions, each drug position being associated with a respective one of said drug outlets; and
- wherein the valve presents, in each selected drug position:
- a drug flow path extending from the associated drug outlet, through the main passageway, and to the outlet of the valve,
- flushing flow path extending from the flushing outlet to the outlet of the valve and comprising a first part not being common with the drug flow path and a second part being common with the drug flow path, and
- a backpriming flow path extending from the flushing outlet to the associated drug outlet and being at least partly common with the first part of the flushing flow path.

According to the inventive concept, there is further provided a method for administering a plurality of drug fluids to a patient using a flushing container containing a flushing fluid, a plurality of drug containers each containing an associated drug fluid and being provided with an associated drug connector line, a valve having valve member which is arranged to be rotated into a plurality of drug positions, each drug position for administering an associated drug fluid, and a primary IV line connected to a patient, said method comprising, for each drug fluid of said plurality of drug fluids:
- rotating the valve member into a selected drug position associated with the drug fluid;
- with the valve being in the selected drug position, backpriming a connector line of a drug container containing the drug fluid by providing a flow of the flushing fluid from the flushing container via the valve and into the secondary connector line;
- thereafter, and with the valve being in the selected drug position, administering the drug fluid by providing a flow of the drug fluid from the drug container containing the drug fluid via the valve to the primary IV line; and
- thereafter flushing the valve by providing a flow of the flushing fluid from the flushing container via the valve to the main IV line.

Preferred embodiments of the valve and the method are set out in the dependent claims.

The valve and the method of the present invention are especially, but not exclusively, useful for performing a multi-drug administering according to procedures being used in the U.S. where initially non-primed secondary lines are backprimed before the secondary infusions are initiated. More specifically, the valve of the present invention makes it possible for a user to perform, with the valve member being positioned in a selected drug position for a selected one of a plurality of drug fluids, both the backpriming of the drug line associated with the selected drug fluid and the administering of the selected drug fluid.

The valve and the method of the present invention are also useful for performing a multi-drug administering according to procedures presently used in other countries, such as in Europe.

As a further advantage, the inventive valve allows a user to also perform a third step of the infusion process—the flushing of the valve and the main IV line after the administering of one drug has been finished—with the valve member being positioned in the same selected drug position as used during backpriming and drug administering.

Since the valve may be positioned in the same drug position when performing all three actions, the valve presents the advantage that the required number of valve operations may be kept to a minimum and also the advantage that a handle of the rotary valve member may be positioned visually aligned with a selected drug inlet for each associated drug fluid during the three steps. The user may thus easily associate each selected valve position with the drug fluid presently being handled, further increasing the overall safety aspect of the procedure.

The inventive valve allows multiple secondary lines to be connected to the valve and allows multiple drug fluids to be administered to the patient, one at a time, without the risk of unintentionally mixing incompatible drug fluids, by using a turn valve configuration where there is no connection between two drug inlets, which also leads to the benefit that back flow valves on the secondary lines become redundant. This is a cost saving for the European system and an additional safety benefit for the U.S. system where backflow valves have been impossible to use, because of the need to back prime the secondary lines.

The inventive valve allows multiple secondary lines to be connected to the valve and allows multiple drug fluids to be administered to the patient, one at a time, without the risk of unintentionally mixing of incompatible drug fluids. The secondary lines do not need to be re-used, but rather a new secondary line is connected to a new drug inlet for each drug fluid. This advantage will reduce the risk of any drug incompatibility of drug residuals within the same secondary line, if this is re-used and re-spiked with a different drug fluid. The risk of re-spiking bags may involve a risk of contamination that may lead to bacteria colonization and could lead to catheter related blood stream infection for the patient, but also the healthcare worker is at higher risk for toxic fumes or spillage.

The inventive valve allows all secondary lines to be connected before patient has arrived, and even the infusion system may be prepared, and all secondary lines to be connected to the valve, in a different room in a sterile environment with good ventilation before use, to increase safety for both patient and healthcare workers.

The valve may preferably be structured and arranged such that different drug fluids never will mix in the valve. Thus, in a preferred embodiment it is not possible to rotate the valve member into a position where different drug inlets of the valve are in fluid contact with each other via the valve.

The inventive valve is structured and arranged in such a way that, in each selected drug position of the valve member, a drug outlet which is associated with the selected drug position is fluidly connected to both the inlet of the main passageway of the rotary valve member and also to the flushing outlet in the housing. This means that in each selected drug position, there is a fluid connection between all three of the associated drug outlet, the main passageway of the valve member and the flushing outlet of the housing. Because of this intended "open structure" of the inventive valve in each selected drug position—which structure allows the user to perform up to three actions for each selected drug fluid with the valve member being positioned in one and the same drug position associated with the selected drug fluid— in order to ensure that a correct fluid (drug fluid or saline fluid) will flow through the valve in each selected drug position, some additional fluid control may be required to ensure that either the drug fluid flows through the valve (during drug administering) or the saline fluid flows through the valve (during backpriming and during flushing).

In some embodiment, such an additional fluid control may be implemented by arranging the saline container on the one hand, and each drug container on the other hand, on different levels in order to create a flow controlling pressure difference. Thus, during drug administering the associated drug container may be held on a higher level than the saline container, and during backpriming and flushing the saline container may be held on a higher level than the drug containers. In an alternative embodiment, such an additional fluid control may be implemented by arranging clamps and/or back check valves on the fluid lines. These embodiments may be combined.

In some embodiments, the valve may further comprise a distribution channel which is arranged to carry the flushing fluid and which is formed at an interface between the housing and the valve member, said distribution channel being circumferentially oriented in relation to the rotational axis and fluidly connected to the flushing outlet. The purpose of the distribution channel is to make it possible to have access to the flushing fluid in each selected drug position of the plurality of drug positions, even if the valve comprises one flushing inlet only. The surfaces defining the circumferentially oriented distribution channel may be formed in combination by one or more surfaces of the housing and one or more surfaces of the valve member. In a preferred embodiment, the distribution channel is formed when the valve member is inserted into the housing cavity during assembly. The distribution channel may be arranged on the same first level as the flushing outlet such that the flushing outlet opens into the distribution channel.

In order to carry the flushing fluid from the distribution channel towards the respective drug outlets of the housing, the valve member may further comprise a transfer channel for carrying the flushing fluid, the transfer channel being fluidly connected to the distribution channel and extending at least partly in the direction of the rotational axis towards the second level. The transfer channel may extend in parallel to the rotational axis or in an inclined orientation. The flushing fluid present in the distribution channel will be in fluid connection with the transfer channel in each one of the drug positions of the valve member. When the valve member is rotated, the transfer channel will thus be rotated together with the valve member.

There are different possibilities of completing the fluid transfer from the circumferential distribution channel to each one of the drug outlets. This fluid transfer will be performed in a direction which is axial, inclined or a combination thereof.

According to a first alternative embodiment for creating a flow path between the flushing outlet to the drug outlets, an outlet of the transfer channel of the valve member may be directly connected, within the valve member, to the main passageway between the inlet and the outlet thereof. In this embodiment, the transfer channel may be formed by a bore in the valve member body or by an at least partly radially open groove or recess which is formed in the circumferential outer surface of the valve member and which is closed by the inner circumferential surface of the housing to complete the shape of the transfer channel. In this alternative, it may be preferred that the outlet of the transfer channel connects to the main passageway in the valve member close to the inlet of the passageway such that, when performing a flushing operation, the flushing fluid enters the main passageway from the transfer channel at the very beginning of the main passageway and, thereby, flushes the entire main passageway towards the outlet thereof.

According to a second alternative embodiment for carrying the flushing fluid to the drug outlets, the housing may further comprise a plurality of flushing recesses formed in the inner circumferential surface of the valve housing, each flushing recess being associated with a selected drug position and extending at least partly in the direction of the rotational axis and being fluidly connected to an associated drug outlet. Each flushing recesses may be axially oriented and angularly aligned with an associated drug opening. In each selected drug position, the drug outlet which is associated with the selected drug position may then be in fluid connection with the flushing outlet via a flow path formed by the distribution channel, the transfer channel and the flushing recess which is associated with the selected drug position. During backpriming, the flushing fluid may then flow, at the second level, directly from a flushing recess and out through an associated drug inlet without passing through any part of the main passageway of the valve member. During flushing, the flushing fluid may flow to the second level via a flushing groove and then enter the inlet of the main passageway from the drug opening which is presently being aligned with the main passageway.

This embodiment may have the advantage to have a main channel inlet that is closed off completely by sealingly engaging the valve house inner surface in an alternative valve position, resulting in a rotational position where no fluid can flow though the valve's outlet.

According to a third alternative embodiment for transferring the flushing fluid to the drug outlets, the transfer channel formed in the valve member may have a first end, which is located on the first level and is fluidly connected to the distribution channel, and a second end, which is located adjacent the second level and which together with the inlet of the main passageway, in each selected drug position, bifurcates the drug outlet associated with the selected drug position. The bifurcation may extend in a direction perpendicular to the rotational axis such that, when viewed radially inwards from a drug outlet, one would see both the outlet of the transfer channel on one axial side of the bifurcation and the inlet of the main passageway on an opposite axial side of the bifurcation. In each selected drug position, the drug outlet which is associated with the selected drug position may then be fluidly connected to the flushing outlet via a flow path formed by the distribution channel and the transfer channel. When performing a flushing operation, the flow path would continue in a U turn at the drug opening around the bifurcation and then into the main passageway of the valve member. This may be useful for priming of drug inlets before use when there is a cap fitted on the drug inlet, and or may be useful if the drug inlet is fitted with a closed system device such as an elastomeric element that is normally closed but opens when e.g. a male luer tip is connected to the drug inlet.

In some embodiments, the distribution channel may extend in a circumferential direction over 360 degrees to form a complete annular distribution channel. In some alternative embodiments, the distribution channel may extend in a circumferential direction less than 360 degrees to form a partial annular distribution channel. The partly annular distribution channel may present two ends, wherein one of the ends may preferably be located at an angular position at which the distribution channel connects to the transfer channel. Thereby, an internal priming of the valve's dead space is obtained before the valve is used, by the flushing fluid pushing any air bubbles present in the distribution channel out of the distribution channel and into the transfer channel, and out of either a drug inlet or out of the valve's outlet before it is connected to the patient, without any risk of an air bubble remaining in the distribution channel, which is thereby primed for all subsequent valve positions.

In some embodiments, the inner circumferential surface of the housing may be in sealing engagement with the outer circumferential surface of the valve member. The inner circumferential surface of the housing and the outer circumferential surface of the valve member may be cylindrical, conical, frusto-conical or combinations thereof.

In some embodiments, the main passageway of the valve member may comprise a first part extending from the inlet of the main passageway towards the rotational axis, and a second part extending coaxially with the rotational axis, from an radially inner end of the first part of the main passageway, towards the outlet of the main passageway. The second part may also extend in a direction not being coaxial with the rotational axis. In other embodiments, the main passageway may extend in any direction between the inlet and the outlet thereof. The outlet of the main passageway is preferably located coaxially with the rotational axis.

In some embodiments, the outlet of the main passageway of the valve member may form the outlet of entire valve, i.e. the fluid would exit from the valve at the outlet of the main passageway without re-entering the housing, and in this case the passageway outlet does not need to be formed coaxially with the rotational axis. In some embodiments, the outlet of the main passageway of the valve member may instead be fluidly connected to an outlet of the valve formed in the housing, and in those cases the outlet is preferably formed coaxially with the rotational axis to avoid unnecessary dead space volume that would need flushing.

In some embodiments, the plurality of drug positions constitute the only rotary positions of the valve member allowing a drug to be administered from a drug inlet to an outlet of the valve. In such embodiments, the only rotary positions of the valve member in which a drug may flow from a drug inlet through the valve would be said plurality of drug positions in which there is also a fluid connection from the flushing outlet to the valve opening. In other words, there would be no "pure" drug positions in which a drug outlet but not the flushing outlet is fluidly connected to the main passageway via the valve.

As to the first and second levels, these may be arranged according to two alternatives. The valve member may typically be provided with a handle for rotating the valve member. According to a first alternative, the first level is located closer to the handle than the second level. In a second alternative, the second level is located closer to the handle than the first level.

In some embodiments, the valve member may be provided with a handle for rotating the valve member, wherein in each selected drug position the handle may be aligned with a drug inlet associated with the selected drug position. An advantage is thereby achieved that a user may visually associate a selected handle position with a drug presently being handled. As an example, when handling a first drug fluid, a user may align the handle with an associated first drug inlet of the valve during the backpriming of an associated first drug line, during the administering of the first drug fluid and during flushing of the valve for any residuals of the first drug fluid.

The inventive method for administering a plurality of drug fluids may be performed according to various embodiments. In some embodiments, the steps of rotating the valve into a selected drug position, backpriming an associated drug line with the flushing fluid, administering an associated drug fluid and flushing the valve with the flushing fluid may be performed as direct sequence, one step directly after the other, while maintaining the valve member in the selected drug position during the backpriming, the administering and the flushing. In some alternative embodiments, the backpriming may be performed for two or more drugs initially, in order to prepare the set-up or system for administering, such as in another room than the room where the patient located. In such embodiments, one and the same selected valve position may be maintained during the subsequent drug fluid administering and flushing for each drug fluid.

In some embodiments, the valve member may further be arranged to be rotated into any selected one of one or more flushing positions, wherein, in each selected flushing position, the inlet of the main passageway is fluidly connected to the flushing outlet but not to any one of the drug outlets. In such embodiments, the flushing may be performed either in the selected drug position (valve rotational position maintained) or in an intermediate "pure" flushing position in which no drug outlet is fluidly connected to the outlet of the valve. If the valve comprises two drug inlets only, only one single flushing position may be needed in such embodiments.

In some embodiments, the valve member may further be arranged to be rotated into any selected one of one or more closed positions, wherein each closed position there is no fluid connection between the drug inlets and the valve outlet, nor any fluid connection between the flushing inlet and the valve outlet.

The different valve positions are preferably predetermined positions and are preferably identifiable by the user. This may be done by the shape of a handle and/or by arranging a tactile or haptic response to a user at each valve position so the operator can sense the correct position ("click indication").

The valve is preferably a disposable product intended for one complete treatment use. The housing and the valve member may be manufactured by means of molding, such as injection molding that is suitable for high production volumes to get the unit cost as low as possible. More specifically, the housing and the valve member may each be manufactured in a single piece.

Terminology

As mentioned above, in the field of intravenous infusion where both a neutral fluid, such as a saline fluid, and one or more drug fluids are to be administered to a patient, the terminology normally used in the art is that the infusion of the neutral fluid is referred to as the primary infusion or the main IV line, whereas the infusion of a drug fluids is referred to as the secondary infusion. This terminology will be used in the present application. However, for the sake of clarity and explanation, the more descriptive terms "saline", "flushing" and "drug" will be used as equivalents to "primary" and "secondary" where appropriate to designate parts of the primary and secondary infusion, different valve positions, different valve parts and different flow paths.

The term "drug fluid" as used herein is to be interpreted in a wide sense and should not be limited to pure drugs. Drug fluids may include various types of cytostatics which are to be infused into the vascular system of a patient intravenously in order to treat her/him from cancer. Other fluids which may be administered may include volume expanders, blood-based products, blood substitutes, medications, nutritional solutions, antibiotics etc.

The terms "flushing fluid" and "saline fluid" are used herein as equivalents. The terms are to be interpreted as comprising any suitable fluid to be administered to the patient and/or for priming/flushing purposes. Especially, the flushing fluid may be a neutral fluid, such as a saline solution.

The term fluid passageway should be construed as including channels in the form of a bore having defined end openings, open recess configurations, or combinations thereof.

The term "backpriming" as used herein is to be construed as an operation performed for removing air from an infusion pathway, especially an initially non-primed secondary line or drug line connected to a drug container containing a drug fluid to be administered, said backpriming being performed by causing a flushing fluid to flow "backwards" or "upstream" into and fill the infusion pathway, thereby removing air there from.

The term "flushing" as used herein is to be construed as the operation performed for cleaning at least the valve or parts thereof from previously administered drugs, especially the main passageway of the valve member.

Other features and advantages of embodiments of the present invention will become apparent to those skilled in the art upon review of the following drawings, the detailed description, and the appended claims.

BRIEF DESCRIPTION OF THE DRAWINGS

The inventive concept, some non-limiting embodiments and further advantages of the inventive concept will now be further described with reference to the drawings.

FIG. 5A illustrates the valve in a first drug position, indicating a backpriming flow path, shown from a perspective view.

FIG. 5B illustrates the valve of FIG. 5A shown in an elevational view.

FIG. 5C illustrates the valve of FIG. 5A shown in a plan view.

FIG. 5D illustrates the valve of FIG. 5A shown in a sectional view taken substantially along the line B-B in FIG. 5B.

FIG. 5E illustrates the valve of FIG. 5A shown in a sectional view taken substantially along the line A-A in FIG. 5C.

FIG. 5F illustrates the valve of FIG. 5A shown in a sectional view taken substantially along the line C-C in FIG. 5B.

FIG. 6A illustrates a valve in the first drug position, indicating a drug flow path, shown from a perspective view.

FIG. 6B illustrates the valve of FIG. 6A shown in an elevational view.

FIG. 6C illustrates the valve of FIG. 6A shown in a plan view.

FIG. 6D illustrates the valve of FIG. 6A shown in a sectional view taken substantially along the line B-B in FIG. 6B.

FIG. 6E illustrates the valve of FIG. 6A shown in a sectional view taken substantially along the line A-A in FIG. 6C.

FIG. 6F illustrates the valve of FIG. 6A shown in a sectional view taken substantially along the line C-C in FIG. 6B.

FIG. 7A illustrates a valve in the first drug position, indicating a flushing flow path, shown from a perspective view.

FIG. 7B illustrates the valve of FIG. 7A shown in an elevational view.

FIG. 7C illustrates the valve of FIG. 7A shown in a plan view.

FIG. 7D illustrates the valve of FIG. 7A shown in a sectional view taken substantially along the line B-B in FIG. 7B.

FIG. 7E illustrates the valve of FIG. 7A shown in a sectional view taken substantially along the line A-A in FIG. 7C.

FIG. 7F illustrates the valve of FIG. 7A shown in a sectional view taken substantially along the line C-C in FIG. 7B.

FIG. 8A illustrates a valve in an optional flushing position, indicating a flushing flow path, shown from a perspective view.

FIG. 8B illustrates the valve of FIG. 8A shown in an elevational view.

FIG. 8C illustrates the valve of FIG. 8A shown in a plan view.

FIG. 8D illustrates the valve of FIG. 8A shown in a sectional view taken substantially along the line B-B in FIG. 8B.

FIG. 8E illustrates the valve of FIG. 8A shown in a sectional view taken substantially along the line A-A in FIG. 8C.

FIG. 8F illustrates the valve of FIG. 8A shown in a sectional view taken substantially along the line C-C in FIG. 8B.

FIG. 18A illustrates an alternative embodiment of a valve member with a recess in the valve member where the back check valve may be fitted, shown in elevational view.

FIG. 18B illustrates the valve member of FIG. 18A, shown in sectional view taken substantially along the line A-A in FIG. 18A.

FIG. 18C illustrates an alternative embodiment of a valve member provided with an integrated back check valve, shown in elevational view.

FIG. 18D illustrates the valve member of FIG. 18C, shown in sectional view taken substantially along the line A-A in FIG. 18C.

FIG. 18E illustrates the valve member of FIG. 18A, shown in perspective view in a first condition before the back check valve is fitted.

FIG. 18F illustrates the valve member of FIG. 18C shown in a second condition with the back check valve fitted in place.

DETAILED DESCRIPTION OF THE PREFERRED EMBODIMENTS

The present inventive concept relates to disposable valves for administration of drug fluids. For example, the drug fluids may include various types of cytostatics which are to be infused into the vascular system of a patient intravenously in order to treat her/him from cancer. Other fluids which may be administered by the present inventive valve include volume expanders, blood-based products, blood substitutes, medications, nutritional solutions, etc.

Valve Structure

Figure 1A:
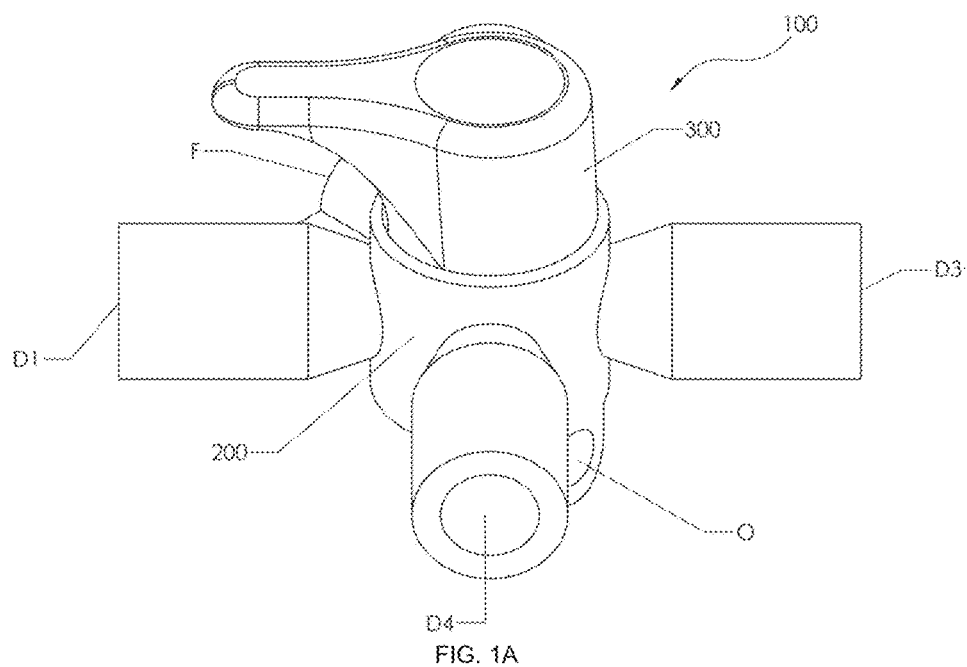
FIG. 1A illustrates an embodiment of a valve shown from a first perspective view.
Figure 1B:
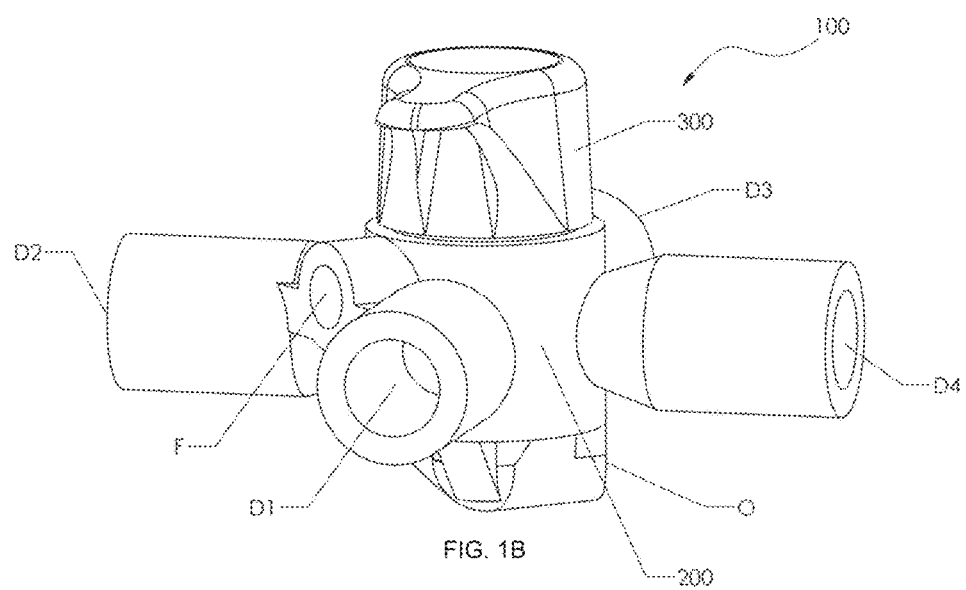
FIG. 1B illustrates the embodiment of the valve of FIG. 1A shown from a second perspective view.
Figure 2A:
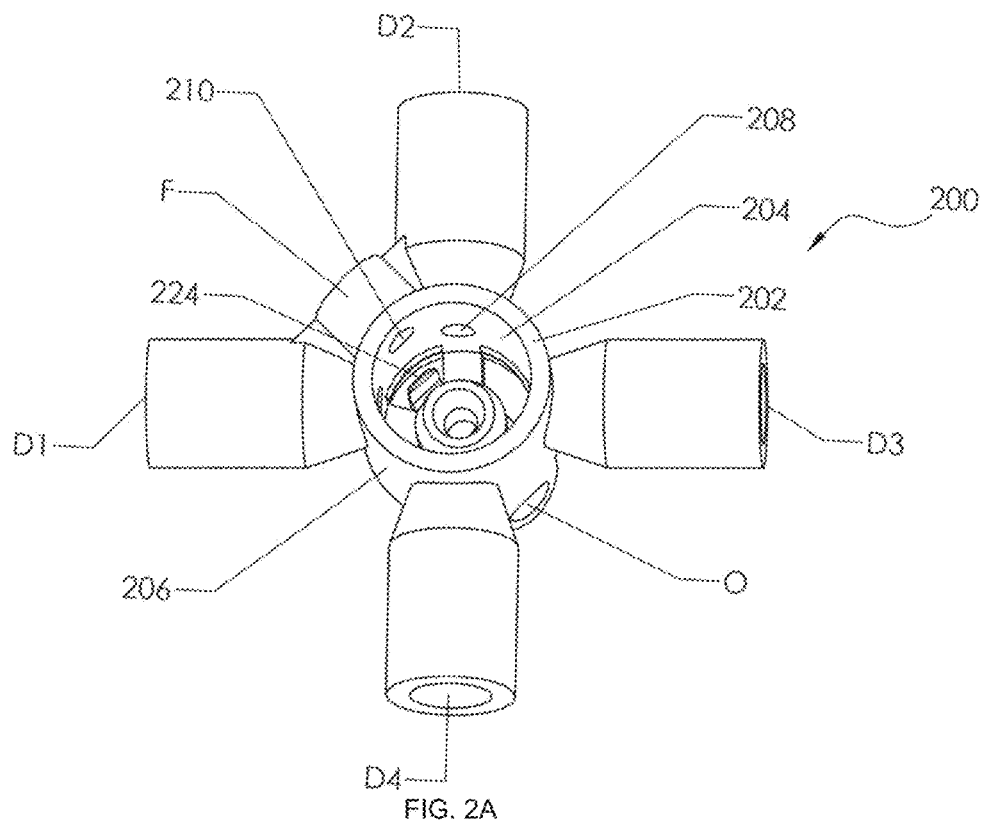
FIG. 2A illustrates the embodiment of a housing shown from a first perspective view.
Figure 2B:
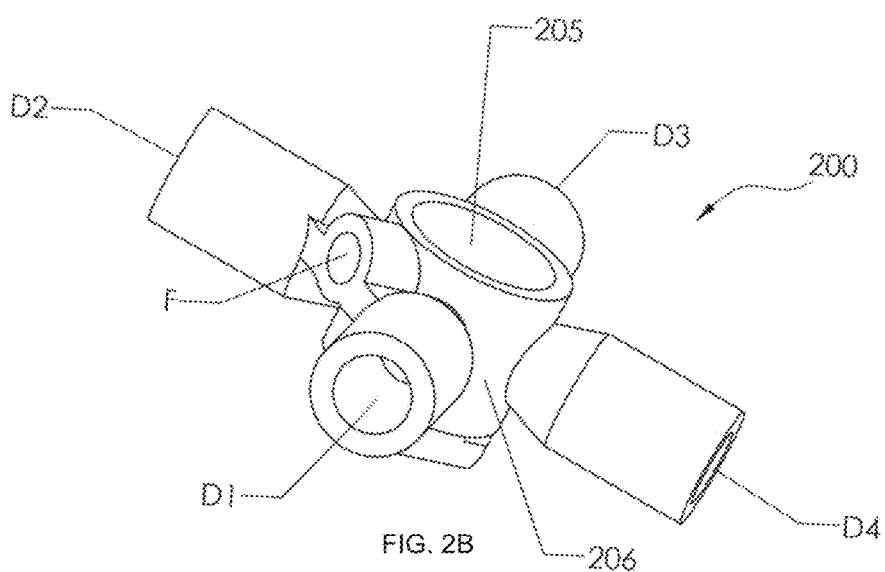
FIG. 2B illustrates the embodiment of the housing of FIG. 2A shown from a second perspective view.
Figure 2C:
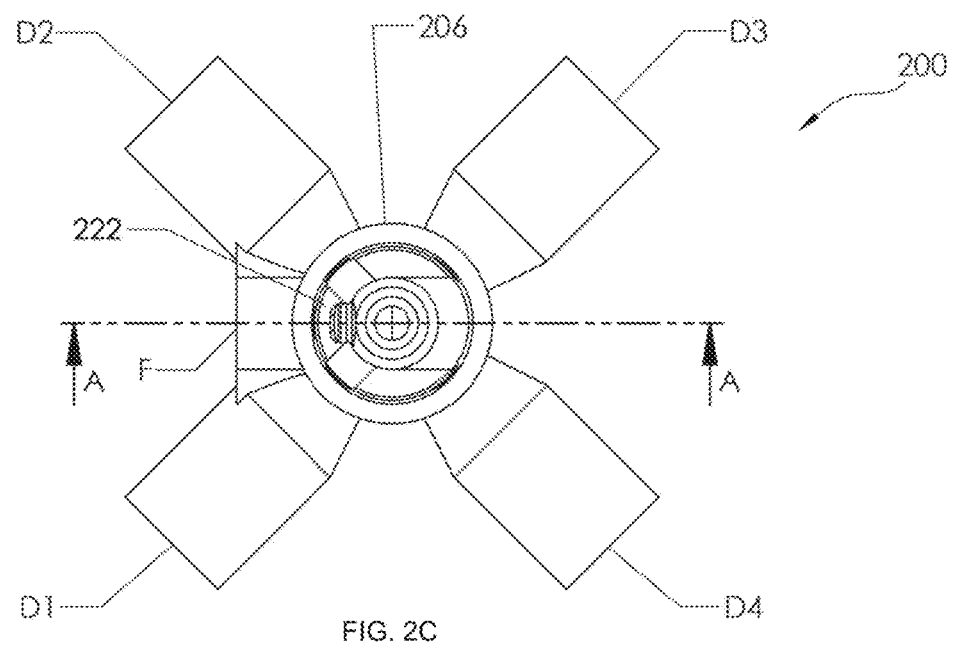
FIG. 2C illustrates the embodiment of the housing of FIG. 2A shown from a plan view.
Figure 2D:
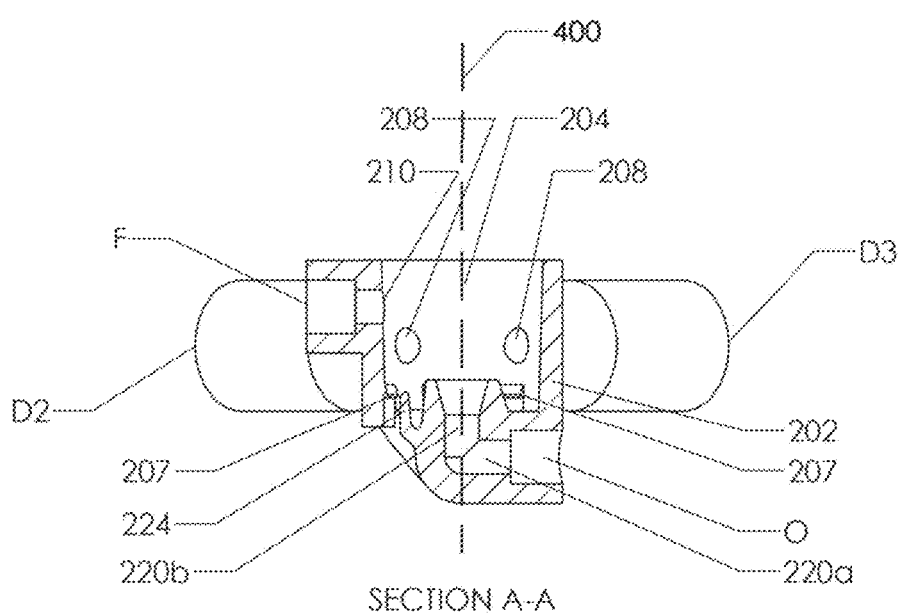
FIG. 2D illustrates the embodiment of the housing of FIG. 2A shown in sectional view taken substantially along the line A-A in FIG. 2C.
Figure 3A:
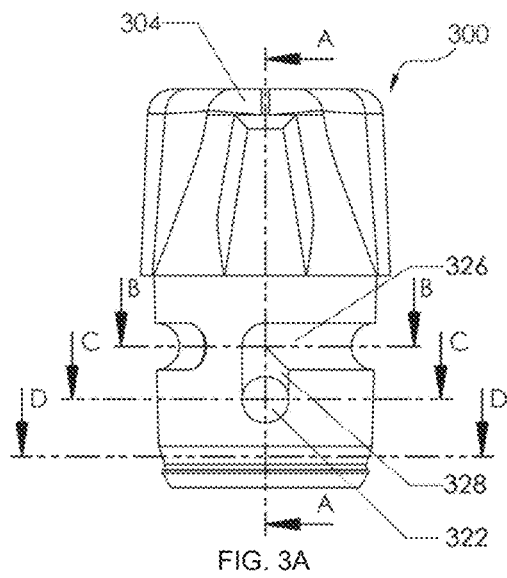
FIG. 3A illustrates a first embodiment of a valve member shown in front elevation.
Figure 3B:
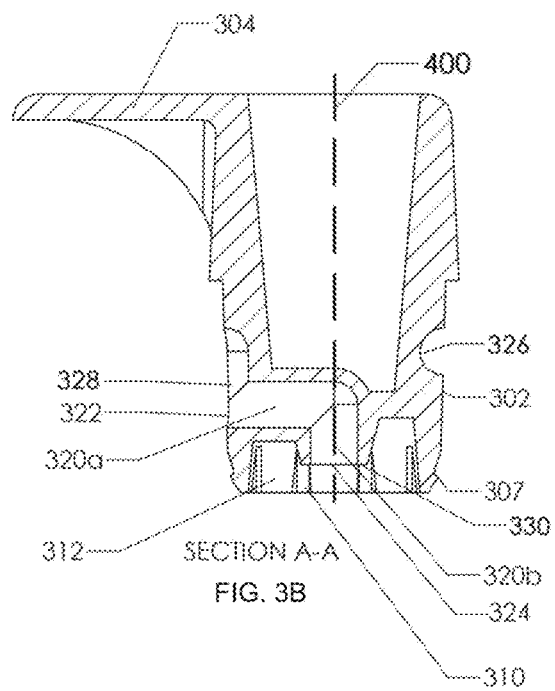
FIG. 3B illustrates a sectional view of the valve member shown in FIG. 3A, taken substantially along the line A-A in FIG. 3A.
Figure 3C:
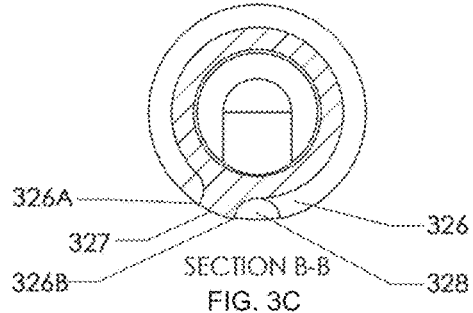
FIG. 3C illustrates a sectional view of the valve member shown in FIG. 3A, taken substantially along the line B-B in FIG. 3A.
Figure 3D:
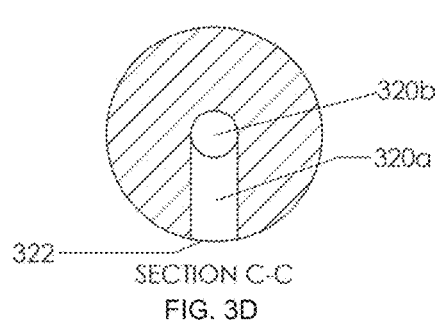
FIG. 3D illustrates a sectional view of the valve member shown in FIG. 3A, taken substantially along the line C-C in FIG. 3A.
Figure 3E:
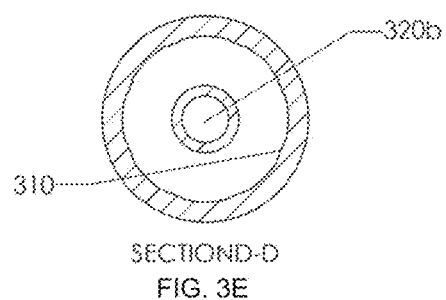
FIG. 3E illustrates a sectional view of the valve member shown in FIG. 3A, taken substantially along the line D-D in FIG. 3A.
Figure 3F:
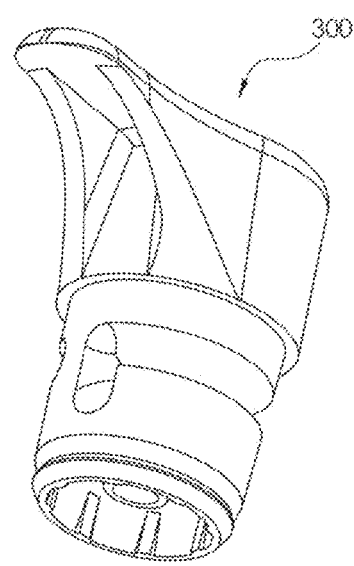
FIG. 3F illustrates a perspective view of the valve member shown in FIG. 3A.
Figure 4A:
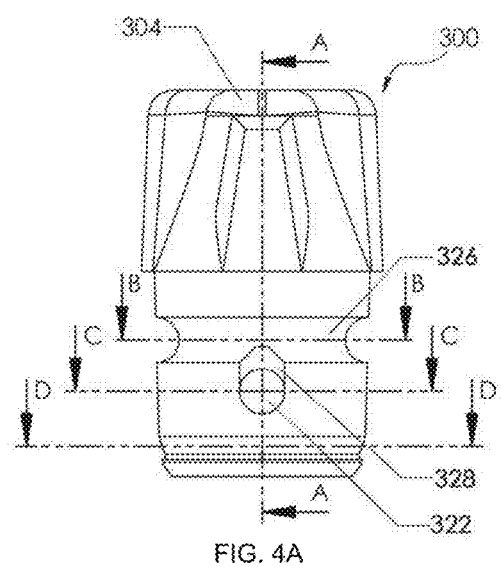
FIG. 4A illustrates a second embodiment of a valve member shown in front elevational view.
Figure 4B:
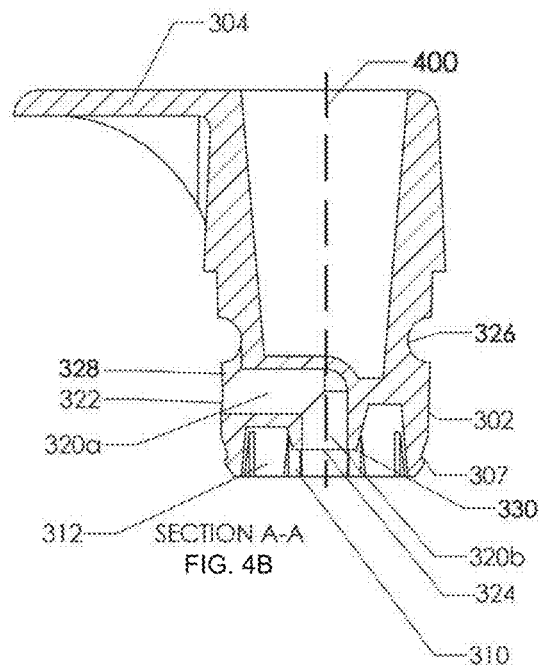
FIG. 4B illustrates a sectional view of the valve member shown in FIG. 4A, taken substantially along the line A-A in FIG. 4A.
Figure 4C:
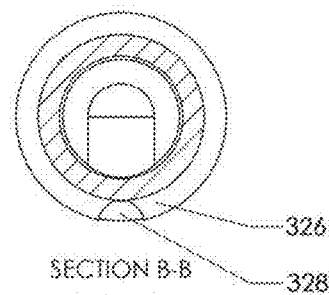
FIG. 4C illustrates a sectional view of the valve member shown in FIG. 4A, taken substantially along the line B-B in FIG. 4A.
Figure 4D:
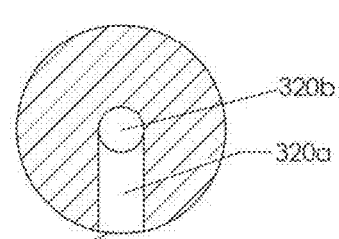
FIG. 4D illustrates a sectional view of the valve member shown in FIG. 4A, taken substantially along the line C-C in FIG. 4A.
Figure 4E:
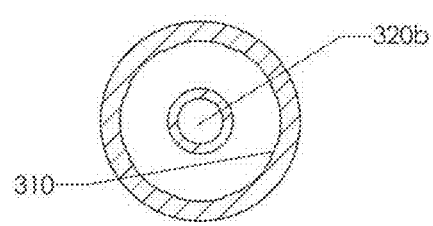
FIG. 4E illustrates a sectional view of the valve member shown in FIG. 4A taken substantially along the line D-D in FIG. 4A.
Figure 4F:
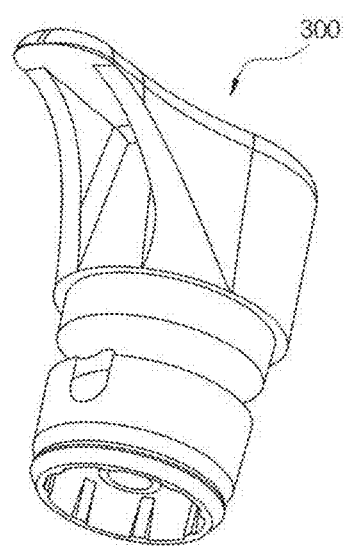
FIG. 4F illustrates a perspective view of the valve member shown in FIG. 4A.

With reference to the drawings, an embodiment of a 4-drug valve or stopcock 100 (FIG. 1A-FIG. 1B) for the administration of up to four different drug fluids is disclosed. While the disclosed embodiment comprises four drug positions other embodiments may comprise a different number of drug positions but more than one. Not all of the possible drug positions of a given valve need to be used at each occasion. For instance, a 4-drug valve as disclosed may be used for administering two drug fluids only.

The valve 100 comprises a cylindrical housing 200 (FIG. 2A-FIG. 2D) and a valve member 300 (FIG. 3A-FIG. 3F and FIG. 4A-FIG. 4F). Detailed views of the assembled valve 100 in different valve positions are shown in FIG. 5A to FIG. 7F.

A cylindrical body of the valve member 300 is rotatably arranged in a cylindrical cavity 205 of the housing 200 in relation to a rotational axis 400. By cylindrical is here meant a cylinder shape with constant radius or cylindrical but possibly with a minor draft needed for the injection mold production. The housing 200 and the valve member body may have shapes other than cylindrical. For example, they may be conical, including one or more frusto-conical parts.

In the assembled valve 100, an outer cylindrical surface 302 of the valve member may be in sealing engagement with an inner cylindrical surface 204 of the housing 200, thereby creating an assembly which is air tight and prevents the flow of fluids at those areas where the surfaces are in sealing engagement. The diameter of the outer surface 302 may be slightly larger than the inner surface 204 in order to provide the sealed engagement.

Alternatively, other ways of providing the sealing engagement are conceivable. In some embodiments, one or more sealing elements (not shown) may be arranged between the housing 200 and the valve member 300. For example, a sealing element may be made of a thin, flexible material which may be fitted snugly between the valve member and the housing. For example, a sealing member may be an O ring.

Reference numeral 207 indicates an inwardly directed flange or rim on the inner surface of the housing 200. Reference numeral 307 indicates a corresponding annular recess in the valve element 300 for receiving the flange 207 in the assembled state in order to maintain the valve member 300 in an axially fixed but still rotatable position in the housing 200. In an alternative embodiment FIG. 15A-FIG. 15C, the flange and the annular recess may be formed at the top part of the housing 200 and not at the bottom part. The recess and flange may also be constructed such that the valve member is provided with the flange and the house is provided with the recess. The flange may also be annularly formed as a protrusion.

The housing 200 and the valve member 300 may be fabricated in any material which does not react chemically to any considerably extent with the drug fluids to be used, and which thereby and also in other aspects is suitable for medical applications. Moreover, the material must be suitable for sterile environments. Examples of materials include plastic materials. The plastic material may be transparent or opaque depending on the medical application.

The housing 200 may be fabricated in the same material as the valve member 300. Alternatively, the housing 200 may be fabricated in a material which is different from that of the valve member 300. In particular, the material of the housing 200 and the valve member may have different hardness. Different hardness may be used for providing tactile feedback during operation of the valve.

Different hardness and different material may also be used for providing improved sealing engagement.

The housing 200 may comprise a housing wall 202 enclosing the inner cylindrical cavity 205 into which the cylindrical valve member body is to be inserted. The cylindrical housing wall 202 may comprise an outer circumferential surface 206 and said inner cylindrical surface 204.

A valve according to the inventive concept may generally comprise a plurality of drug inlets D1, D2, etc. and a single flushing inlet F, all arranged at the outer housing surface 206. As disclosed in this embodiment, a single flushing inlet F arranged on a first level L1 and there may be four drug inlets D1 to D4 arranged on a second level L2 with respect to the rotational axis axially below the flushing inlet level L1.

Each one of the four drug inlets D1 to D4 is fluidly connected to an associated drug outlet 208 which opens into the housing cavity 205. Each drug inlet D1 to D4 may be integrally formed with the cylindrical housing wall 202 and shaped as a pipe or a stud. As in this embodiment, the four drug outlets 208 may be angularly spaced at 90 degrees about the rotational axis 400.

The flushing inlet F may be arranged, in the circumferential direction, between two of the drug inlets and it opens into the inner housing cavity 205 at a separate flushing outlet 210. As for the drug inlets D1 to D4, the flushing inlet F may be integrally formed with the cylindrical housing wall 202 and be shaped as a pipe or stud.

As disclosed in this embodiment, the single flushing outlet 210 on the one hand and the four drug outlets 208 on the other hand may be arranged on different levels with respect to the rotational axis 400. In the disclosed embodiment, the flushing outlet 210 is located on the first level L1 and the drug outlets 208 are located on the second level L2 different from the first level L1. The purpose of having the drug outlets 208 arranged on a different level (L2) is to be able to have access to the flushing fluid in each one of the plurality of drug positions, as will be described in detail.

In the disclosed embodiment, the first level L1 is the upper level in the drawings being located closer to a handle 304 of the valve member 300 than the second level L2. It is possible to design the valve 100 with the levels L1 and L2 being axially reversed.

As disclosed in the present embodiment, the flushing inlet F may be arranged on the first level L1 and the drug inlets D1 to D4 may be arranged on the second level L2, whereby associated passageways or channels through the housing wall 202 would be radially oriented. In other embodiments, the passageways through the housing wall 202 do not have to be exactly radially oriented, allowing for different axial positions of the flushing inlet F and the drug inlets D1 to D4 than the positions shown in the drawings.

In general, a valve member of a valve according to the inventive concept is arranged to be rotated into any selected one of a plurality of drug positions. In the disclosed embodiment, there are four drug positions, each drug position being defined by the angular positions of an associated drug outlet 208. Each drug position may be defined as a valve position in which the inlet 322 of the main passageway 320 is aligned with or registered with a drug outlet 208 associated with the drug position.

The valve 100 comprises an outlet which is arranged to be connected to a downstream part of a primary IV line to be connected with a patient. The outlet of the valve 100 may be formed by the housing 200 or by the valve member 300. In the present embodiment, the outlet is formed in the housing 200. Specifically, the bottom part of the housing 200 may include an outlet O which is fluidly connected to the inner cavity 205 of the housing by means of a bottom channel 220 having a central bottom opening 222 positioned coaxially with the rotational axis 400. The bottom channel 220 may compromise of two parts, including one part 220a extending at least radially outwards from the rotational axis and one part 220b extending at least in the direction of the rotational axis 400.

The housing 200 may be provided with a resilient lip 224, which in this embodiment is integrally formed with the housing 200 at one side of the bottom opening 222 and which is arranged to cooperate with the valve member 300 for providing a tactile response to the user indicating different valve positions. The construction of a tactical response function may be achieved by a protrusion or a recess in the housing to interact with the valve member.

In use, a neutral fluid, such as a saline solution, or equivalently a saline fluid, may be led into the flushing inlet F by means of an upstream part of a main IV line. This neutral fluid, termed "flushing fluid", may comprise a sterile solution of sodium chloride (NaCl). The flushing inlet F may be provided with a connection device (not shown) for connection with the flushing line or it may be glued to the flushing line. Connection devices may comprise male and female Luer connectors. Other connector types may be used.

The valve member 300 of the present embodiment will now be described more in detail with reference FIG. 3A to FIG. 4F illustrating a first and a second embodiment, respectively, of the valve member 300. Identical reference numerals being used for identical or similar parts of the two embodiments.

A handle 304 integrally formed with the valve member body allows the valve member 300 to be rotated by a user into different valve positions, especially into each one of the plurality of drug positions. In this embodiment, the valve positions comprise at least the four drug positions described above. The handle 304 may have a radial extension allowing the user to identify a selected valve position. This is schematically illustrated in FIG. 8A to FIG. 9C for a first and a second drug position, respectively, in which drawings the handle 304 is depicted as a thick bold line aligned with a selected one of the drug inlets D1 to D4.

In the assembled valve, the resilient lip 224 at the housing bottom may be operatively engaged with a contoured circumferential surface 310 of a bottom groove 312 of the valve member 300 in order to provide a tactile response to the user when the valve member is rotated into a selected valve position.

In some embodiments, the contoured circumferential surface 310 and the resilient lip 224 may be formed as a protrusions, notches, grooves or recesses with smooth or sharp edges to create a forced clockwise rotation, or a forced clock-wise rotation with a possibility to turn one position back from a flushing position to a previous drug position.

An object of the invention is to make it possible for the user, such as a nurse, to perform the administration of multiple drug fluids in a simple and safe manner. To this end, it may be preferred that the radial extension of the handle 304, in each selected drug position of the valve member 300, is aligned with an associated drug inlet D1 to D4. The tactile means described above may optionally be used to obtaining a correct alignment of the valve member 300.

The cylindrical valve member body, being rotatably and sealingly arranged in the housing cavity 205, is provided with a main fluid passageway 320 having an inlet 322 arranged at the outer cylindrical valve member surface 302 and an outlet 324 arranged coaxially with the rotational axis 400 at the bottom 330 of the valve member 300. In a preferred embodiment as disclosed, the inlet 322 and the outlet 324 constitute the only inlet and outlet, respectively, of the main passageway 320, in order to ensure a complete flushing thereof as will be described below.

The main passageway 320 may be formed by a first part 320a extending from the inlet 322 of the main passageway 320 towards the rotational axis 400, and a second part 320b extending coaxially with the rotational axis 400 towards the outlet 324 of the main passageway 320. As disclosed, the main passageway 320 may be in the form of a closed tubular channel with the inlet 322 and outlet 324 in the form of defined openings. The inlet opening 322, the tubular channel 320 and the outlet opening 324 may all have the same or essentially the same cross section in order to obtain a laminar fluid flow through the main passageway. The inlet opening 322 of the main passageway 320 and each one of the drug outlets 208 of the housing 200 may have identical or matching cross sections which are mutually aligned in each selected drug position. In other embodiments, the main passageway may be in the form of an open recess or groove.

A feature of the valve 100 is that in each selected drug position, the flushing outlet 210 is fluidly connected to the drug outlet 208 associated with the selected drug position. To this end, the valve 100 is provided with a distribution of the flushing fluid in a circumferential direction with respect to the rotational axis 400.

In the disclosed embodiment, the circumferential distribution of the flushing fluid is accomplished by means of a circumferentially oriented distribution channel 326, which is arranged on the first level L1 and is fluidly connected to the flushing outlet 210. Thus, in this embodiment, the flushing outlet 210 of the housing 200 opens into the distribution channel 326.

In general, the distribution channel 326 will normally be formed in the interface between the housing 200 and the valve member 300. In the disclosed embodiment, the distribution channel 326 is formed by a groove in the valve member, said groove being radially closed by the inner surface 204 of the housing 200. It would also be possible to form the distribution channel 326 by a combination of a stationary lower curved surface formed in the housing 200 and a rotatable upper curved surface formed in the valve member 300. Such an embodiment may be preferred if the valve should have the possibility of closed valve positions mentioned earlier.

In the embodiment shown in FIG. 3A-FIG. 3F, the distribution channel 326 extends in a circumferential direction less than 360 degrees to form a partial annular distribution channel having a first end 326A and a second end 326B, wherein the valve member 300 presents a wall portion 327 located circumferentially between the two ends 326A and 326B. The wall portion 327 will move together with the valve member 300 in all rotational positions.

In an alternative embodiment, the wall portion 327 in the partly annular distribution channel may be formed by the housing 200, and is in such embodiments the wall portion is stationary for all rotary positions.

In the alternative embodiment shown in FIG. 4A-FIG. 4F, the distribution channel 326 extends in a circumferential direction over 360 degrees to form a complete annular distribution channel.

The distribution channel 326 may also be formed at or on the bottom of the valve house when the valve house is constructed with a closed bottom 230, as shown in FIG. 15A to FIG. 16C.

In the following, only the embodiment in FIG. 3A-FIG. 3F will be described. As shown in FIG. 3A-FIG. 3F, the valve member 300 further comprises a transfer channel 328 for carrying the flushing fluid, the transfer channel 328 being fluidly connected to the distribution channel 326 and extending in the direction of the rotational axis 400 from the first level 1 to the second level L2. As best shown in the cross-section B-B in FIG. 3A-FIG. 3F, an upper inlet end of the axial transfer channel 328 connects to the distribution channel 326 close to the end 326B if the wall portion 307 of the partly annular channel is formed by the valve member 300. If the wall portion 207 of the partly annular channel is formed by the housing 200, the transfer channel connects to the distribution channel close to the end 226B in one rotational position. Thereby, in the priming phase of the valve and when the transfer channel is positioned in relation to the flushing outlet 210 on the other side of the wall portion 327, any air bubble residing in the distribution channel 326 will be effectively pushed out from the distribution channel 326 by the flushing fluid and into the transfer channel 328. Subsequent rotational positions may then have a primed distribution channel. Thus, the purpose of making the distribution channel only partly annular according to the embodiment in FIG. 3A-FIG. 3F is to prevent air bubbles in the distribution channel 326 and to create zero dead space within the valve. This technique may optionally be used in other types of multi-drug valves also.

The lower end of the transfer channel 328 at the second level L2 is connected to the main passageway 320 close to the inlet opening 322 thereof. Accordingly, when rotating the valve member 300, the main passageway 320 and the transfer channel 328 rotates together with the valve member 300 and are constantly in fluid connection with the flushing outlet 210 via the distribution channel 236.

Possible Flow Paths in a Selected Drug Position

Figure 9A:
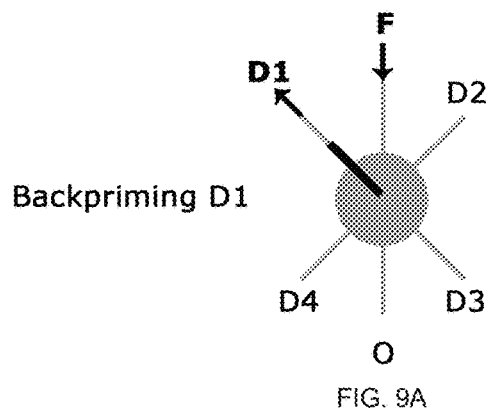
FIG. 9A schematically illustrates a first flow path in the first drug position.
Figure 10A:
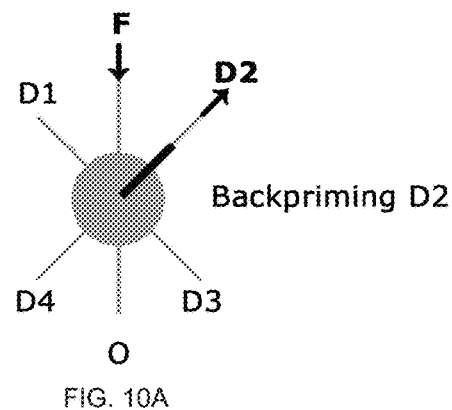
FIG. 10A schematically illustrates a first flow path in a second drug position.
Figure 9B:
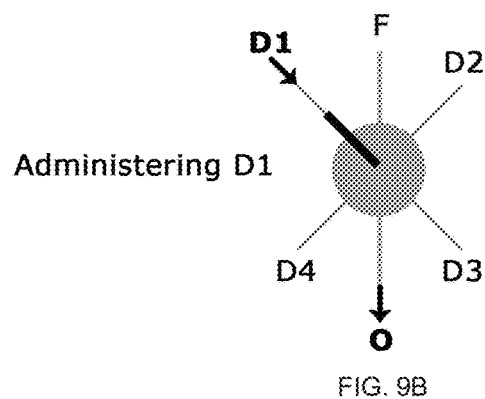
FIG. 9B schematically illustrates a second flow path in the first drug position.
Figure 10B:
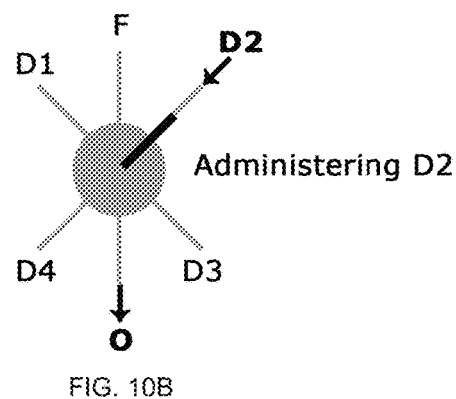
FIG. 10B schematically illustrates a second flow path in a second drug position.
Figure 9C:
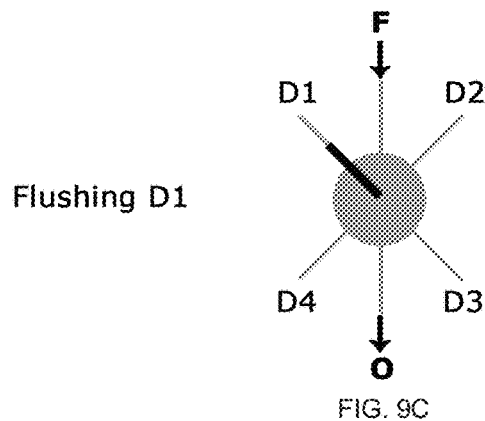
FIG. 9C schematically illustrates a third flow path in the first drug position.
Figure 10C:
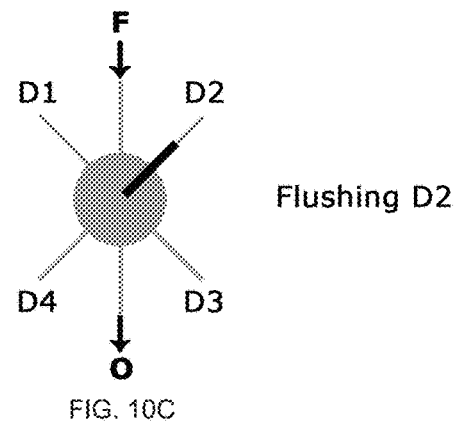
FIG. 10C schematically illustrates a third flow path in a second drug position.

Three different possible flow paths of the valve 100 in a drug position will now be described with reference to especially FIG. 5A-FIG. 7F which show the valve 100 in a first selected drug position of four possible drug positions. In FIG. 5A-FIG. 7F, the flow path described is indicated by a sequence of small unfilled circles for the neutral fluid and filled circles for a drug fluid. In order to increase the understanding, FIG. 9A-FIG. 9C illustrates in an very schematically way where each one of the three flow paths enters into and exits from the valve 100 in the first drug position. Corresponding flow paths for a second selected drug position are schematically illustrated in FIG. 10A-FIG. 10C.

Backpriming Flow Path

FIG. 5 schematically illustrates a backpriming flow path FP of a neutral flushing fluid through the valve 100 for performing a backpriming of a drug line (not shown), the drug line being connected at one end thereof to the first drug inlet D1. The backpriming flow path FP of the flushing fluid will be as follows in FIG. 5:

Flushing inlet F→Flushing outlet 210 on level L1→Into and along distribution channel 326 to the inlet of transfer channel 328→Along transfer channel 328 to level L2→Into the main passageway 320 close to the inlet 322 thereof→"Backwards" out through the drug outlet 208 associated with the first drug position-→"Backwards" out through the drug inlet 210→Backpriming of the drug line.

Drug Administering Flow Path

FIG. 6 schematically illustrates a drug flow path FP of a first drug fluid through the valve 100 for administering the first drug fluid to a patient, the drug fluid being contained in a drug container connected via drug line to the first drug inlet D1, and the outlet O being connected to a main IV line connected to a patient. The drug fluid flow path FP of the first drug fluid will be as follows in FIG. 6:

First drug inlet D1→Drug outlet 208 on level L2→Inlet 322 of the main passageway 320→Through the main passageway 320 to the outlet 324→Outlet O.

Flushing Flow Path

FIG. 7 schematically illustrates a flushing flow path FP of a neutral flushing fluid through the valve 100 for performing a flushing of the valve 100 in order to remove residuals of the first drug fluid before administering a subsequent drug fluid. The flushing flow path FP of the flushing fluid will be as follows in FIG. 7:

Flushing inlet F→Flushing outlet 210 on level L1→Into and along the distribution channel 326 to the inlet of the transfer channel 328→Along the transfer channel 328 to level L2→Into the main passageway 320 close to the inlet 322 thereof→Through and flushing the main passageway 320 to the outlet 324→Outlet O.

It will be noted that the backpriming flow path in FIG. 5A-FIG. 5F and the flushing flow path in FIG. 7A-FIG. 7F share the part of the flow paths which extend from the flushing inlet F via the distribution channel 326 to the outlet of the transfer channel 328. It will also be noted that the downstream part of the flushing flow path in FIG. 7A-FIG. 7F covers or is common with the entire drug flow path inside the main passageway to flush the latter from drug residuals.

Flushing Flow Path in a Flushing Valve Position

The disclosed embodiment of the valve 100 may also be turned into a number of "pure" flushing positions, in addition to the four drug positions described above. FIG. 8A-FIG. 8F discloses the valve 100 where the valve member 300 is in such a "pure" flushing position. The flushing position is in this embodiment a rotational position in-between two drug positions. In a flushing position, the inlet 322 of the main passageway 320 is closed by the inner surface 204 of the housing 200 and all drug outlets 208 are closed by the outer surface 302 of the valve member 300. As a result, no drug fluid may enter the main passageway 320 in a "pure" flushing position. However, the flushing outlet 208 is still in fluid contact with the main passageway 320 via the distribution channel 326 and the transfer channel 328. Thereby, the flushing fluid may flow through the main passageway 320 and out of the outlet O as indicated in FIG. 8A-FIG. 8F.

Figures 11A, 11B:
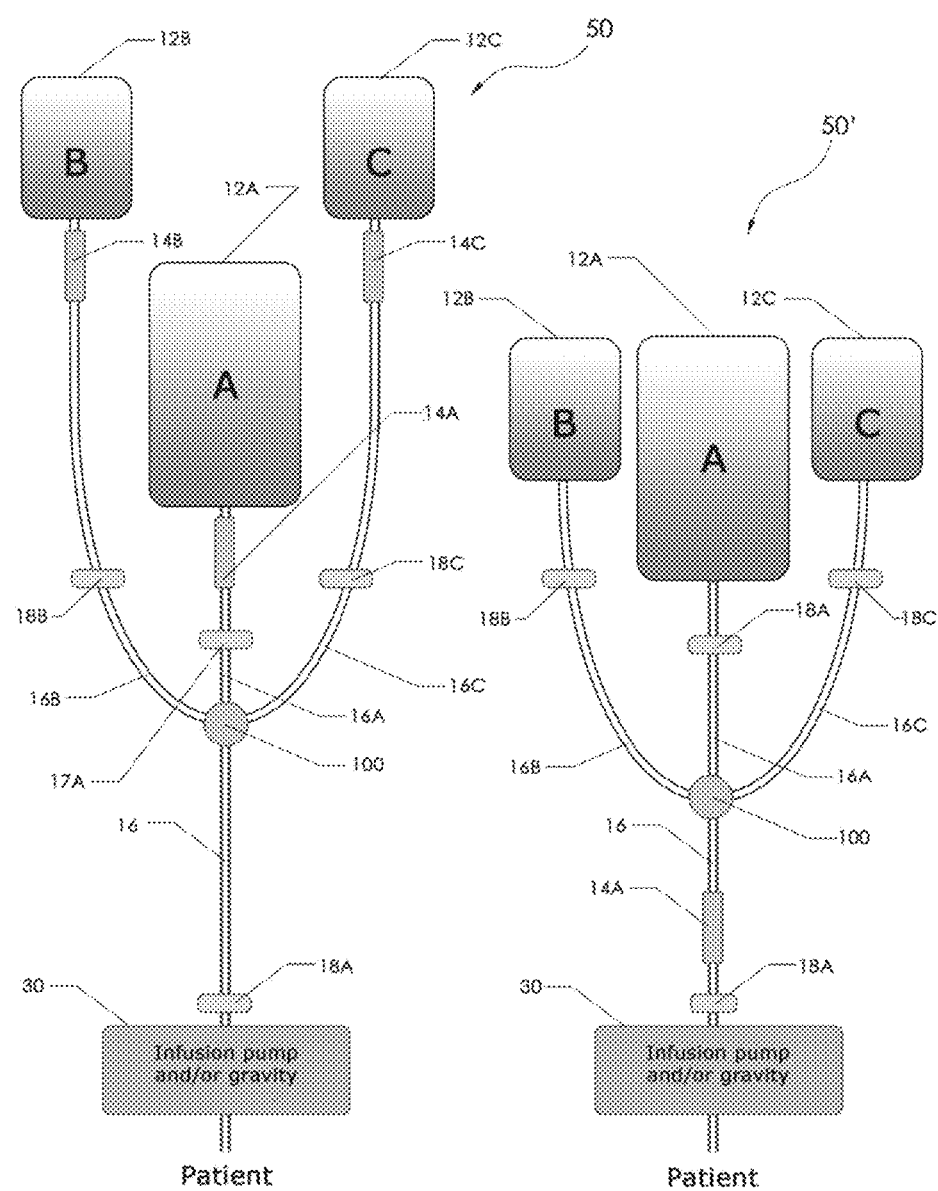
FIG. 11A schematically illustrates IV infusion systems of U.S. type comprising a valve according to an embodiment of the invention.
FIG. 11B schematically illustrates IV infusion systems of European type comprising a valve according to an embodiment of the invention.
Figure 12:
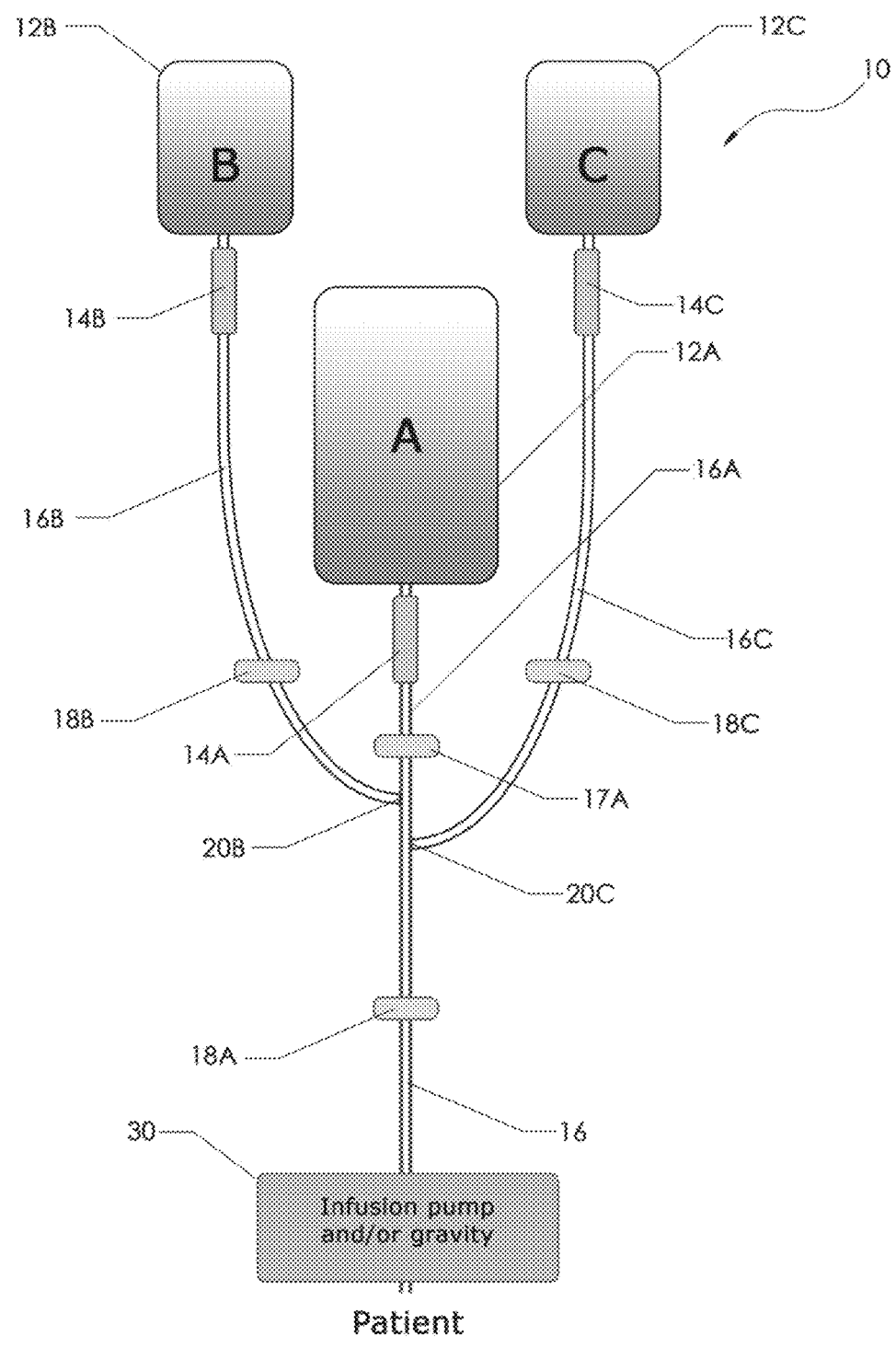
FIG. 12 schematically illustrates a known IV infusion system of U.S. type.
Figure 13:
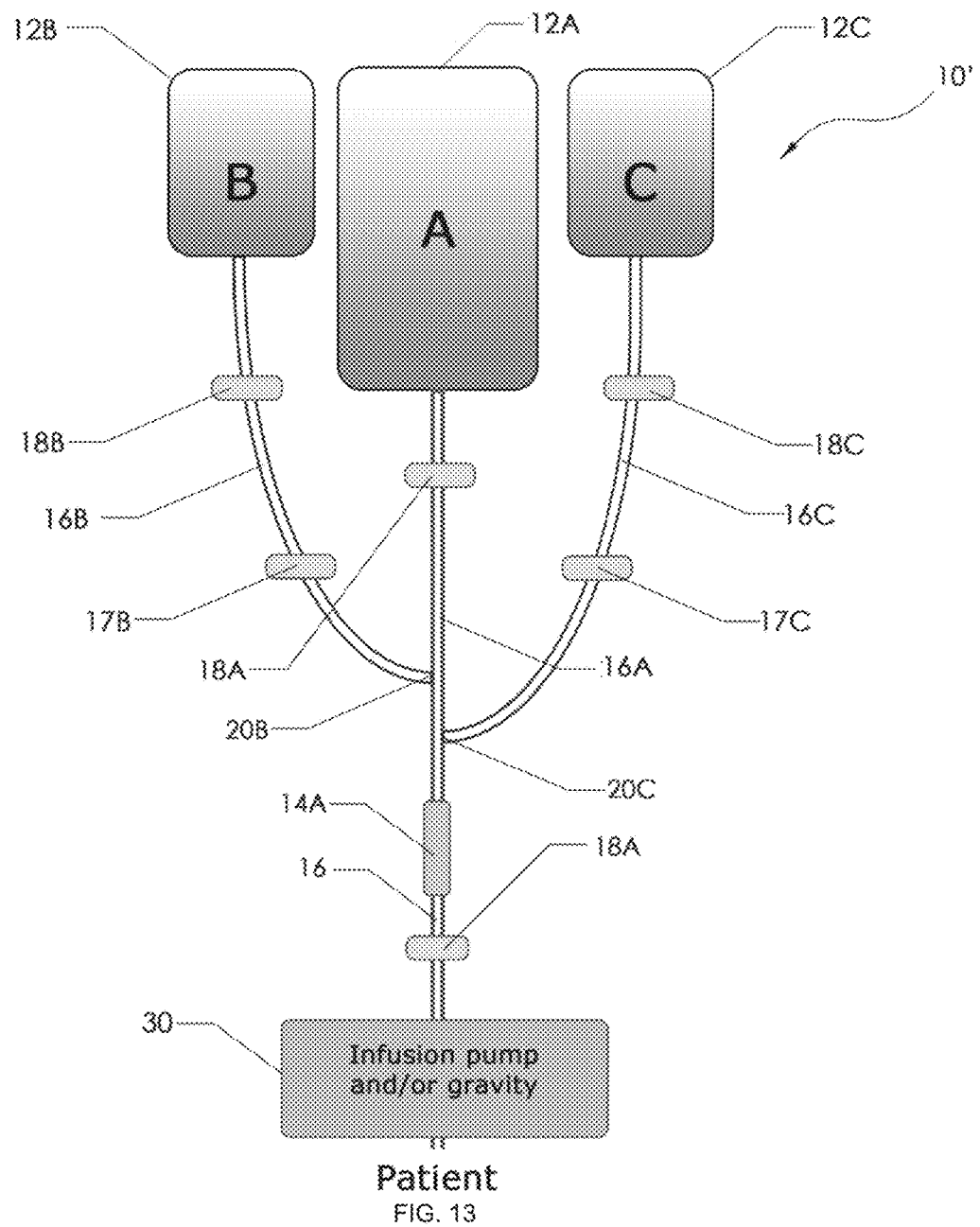
FIG. 13 schematically illustrates a known IV infusion system of European type.
Figure 14A:
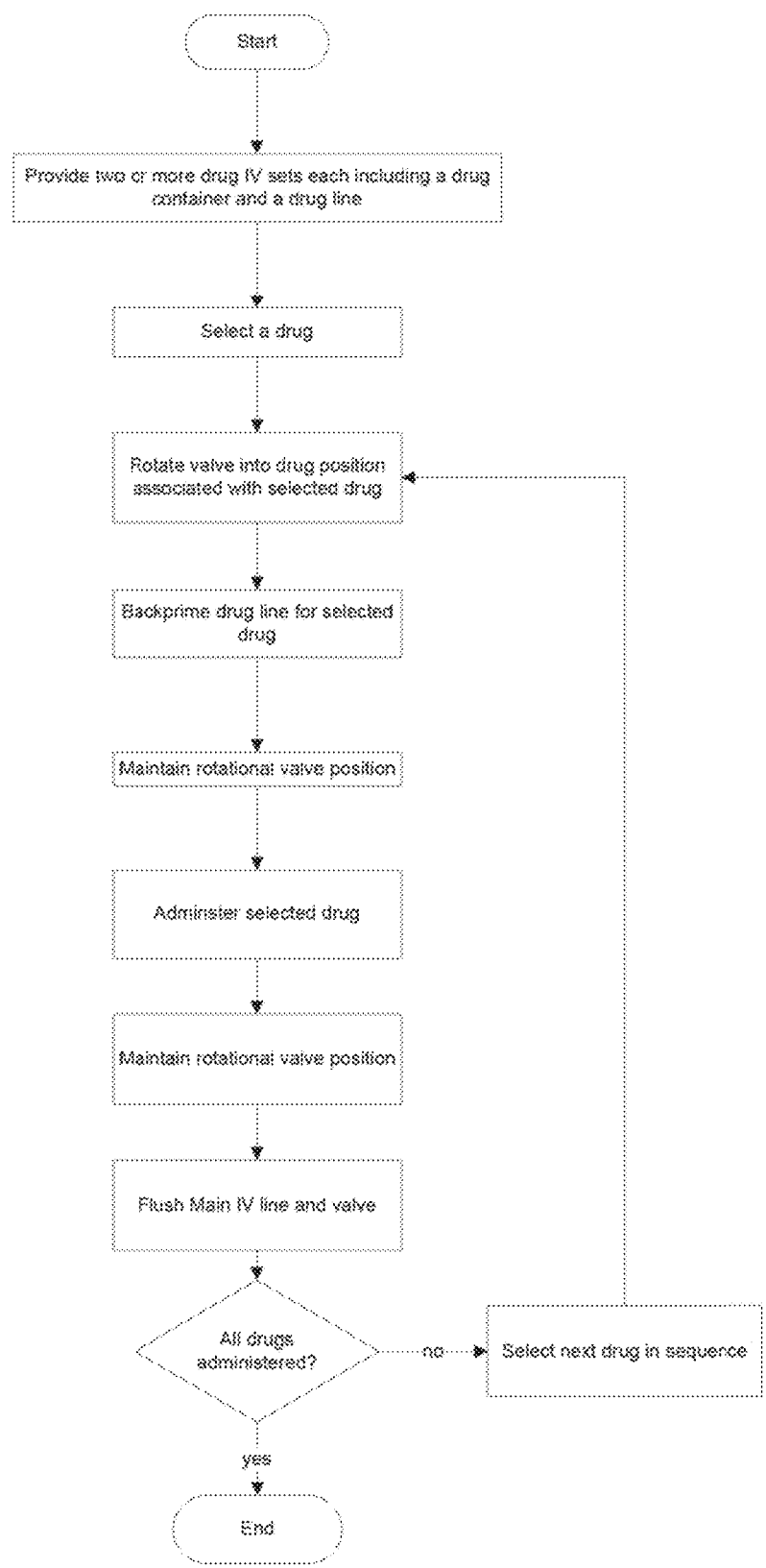
FIG. 14A is a flow chart illustrating a first alternative method of using a valve according of the invention.
Figure 14B:
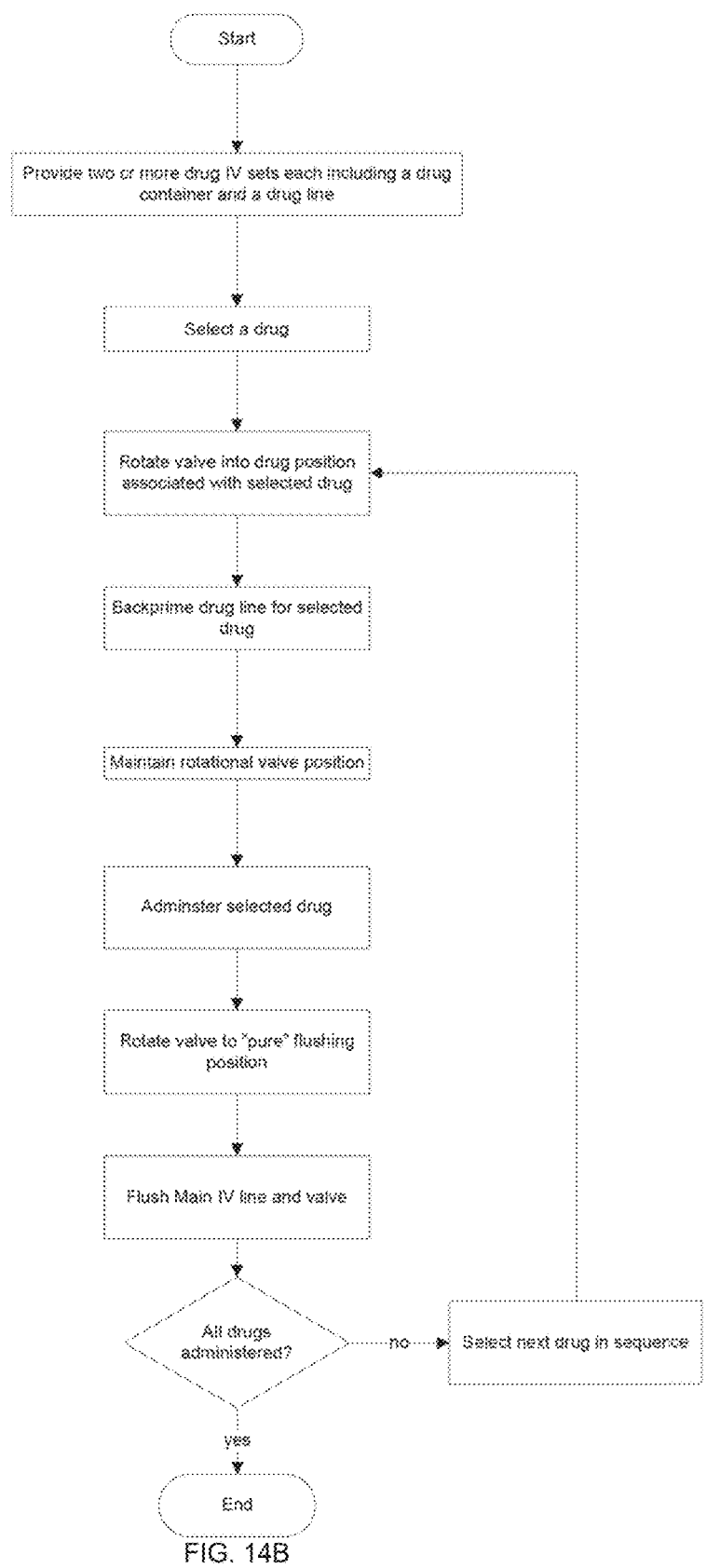
FIG. 14B is a flow chart illustrating a second alternative method of using a valve according of the invention.
Figure 14C:
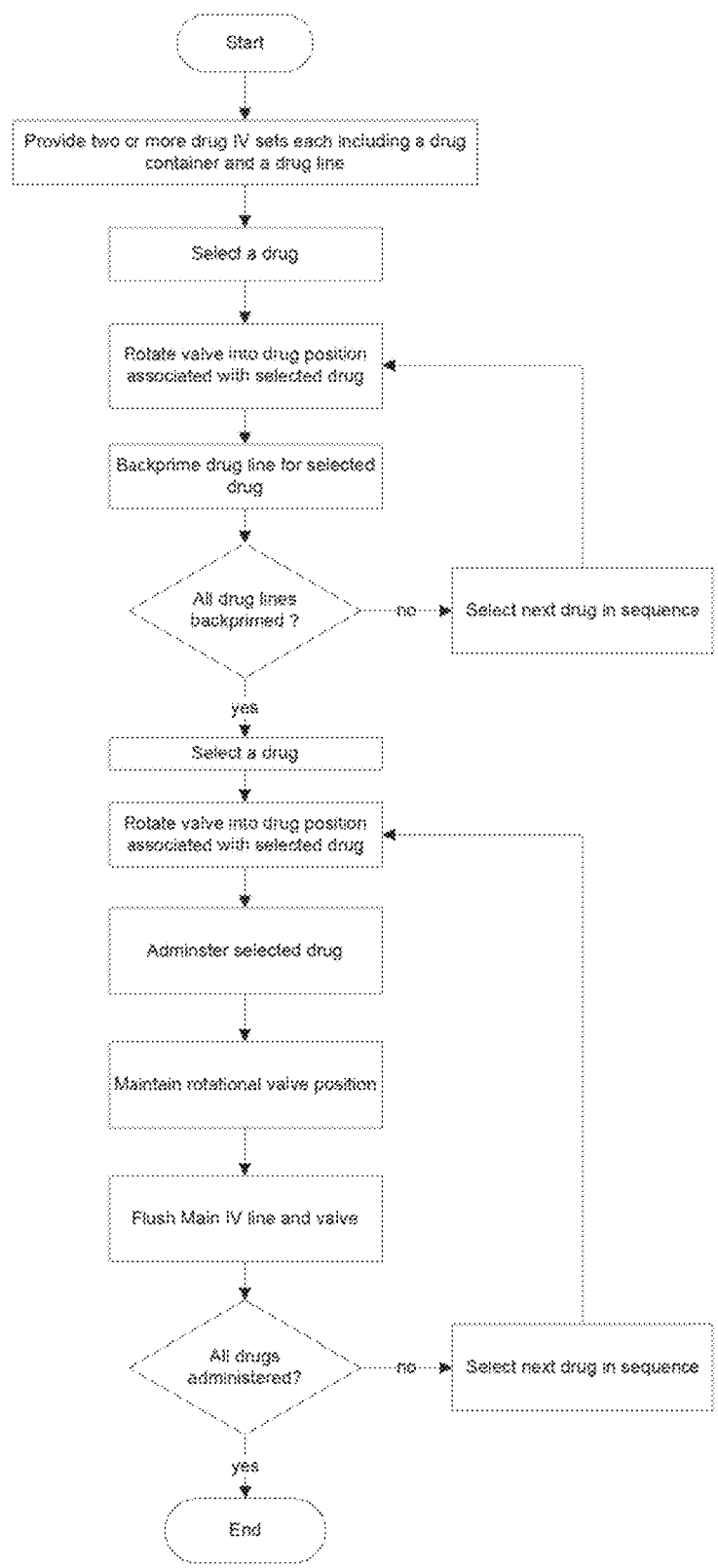
FIG. 14C is a flow chart illustrating a third alternative method of using a valve according of the invention.

IV Therapy System Provided with a Valve According to an Embodiment of the Invention Reference is now made to FIG. 11A and FIG. 11B which schematically illustrate a "U.S. embodiment" 50 and a "European embodiment" 50', respectively, of an IV therapy system including a valve 100 according to an embodiment of the invention.

Where appropriate, the same reference numerals as used for the prior-art systems disclosed in FIGS. 12 and 13 are used also for the systems shown in FIG. 11A and FIG. 11B. The U.S. embodiment 50 in FIG. 11A would probably be more suitable for use in the U.S. since a U.S. user thereof would probably be familiar to a certain extent with the general sequence of actions in using the system 50.

Each system 50 and 50' in FIG. 11A and FIG. 11B comprises a valve 100 according to an embodiment of the invention. The valve 100 is arranged on a main IV line 16. In the U.S. system 50, the main drip chamber 14A is located upstream of the valve 100 on the upper main line 16A and may be integrated with a spike to connect to the container 12A. There may also be a back check valve 17A located upstream the valve 100 but downstream the drip chamber 14A. A clamp to control flow rate, such as a roller clamp, may located downstream the valve 100. In an alternative setup, a roller clamp may be used upstream the valve 100 to control the flow rate of the primary container alone. In yet another alternative embodiment, there may be no clamps to control flow rate, and instead the system may include a slide clamp or a pinch clamp to fully open or fully close the fluid flow. Such an embodiment may be used when the flow rate is controlled by an infusion pump.

In the European system 50', the main drip chamber 14A is located downstream of the valve 100 and the main line is connected to the container 12A with a spike, a clamp is located upstream of the valve 100 on the main line to control the primary fluid and is normally a fully open or a fully closed clamp, such as a slide clamp or a pinch clamp but may be a roller clamp. A roller clamp may be provided downstream of the valve 100 to control the flow rate. If the flow rate is controlled by an infusion pump instead, this roller clamp may be replaced by a slide clamp or a pinch clamp to fully open or fully close the fluid flow.

A first drug IV set 16B and a second drug IV set 16C are connected to a main IV set 16 by means of the valve 100. The upstream line 16A of the main IV set 16 is connected to the flushing inlet F of the valve 100. The first and second drug IV sets 16B and 16C are connected to the first drug inlet D1 and the second drug inlet D2, respectively, of the valve 100. A downstream part of the main IV set 16 is connected to the patient, optionally via an infusion pump 30.

Infusion pumps may be used on the secondary lines 16B, 16C and/or on the upper main line 16A, to control the flow rate of each line individually in the U.S system setup as well as in the European system setup, when a back check valve 17A is used on the upper main line 16A.

Backpriming of the U.S. System

In using the U.S. system 50, backpriming of a (secondary) drug line of each drug IV set may be performed in the following sequence, described for the first drug IV set 16B as an example:

The first drug container 12B is spiked.

The first drug line 16B is then connected to the first drug inlet D1 of the valve 100, optionally using a Luer connection.

The valve member 300 of the valve 300 is rotated by means of the handle 304 into the first drug position (FIG. 5A to FIG. 7F) such that the handle 304 is in a position where it is aligned with or pointing over the first drug inlet D1 connected to the drug line which is to be backprimed.

The clamp 18B on the drug line 16B is opened (if present).

The first drug container 12B is lowered to a level below the flushing container 12A, thereby creating a hydrostatic pressure difference to initiate the backpriming.

The secondary drug line 16B is then backprimed up to half the volume in the drug drip chamber 14B.

When the backpriming of the drug line 16B is complete, the clamp 18B on the drug line 16B is closed and/or the container of the back primed secondary line is held higher than the primary container. As an alternative, the handle 304 is just rotated to the next valve position to close off the secondary flow at the first drug inlet D1.

Preparing the European System

In using the European system 50', handling of the drug IV sets may be performed in the following sequence, described for the first drug IV set 16B as an example. It will be noted that in the European system 50', there are normally no dripping chambers on the drug lines.

The first drug line 16B, which normally would be pre-filled with a neutral solution, is connected to the first drug inlet D1 of the valve 100, optionally using a Luer connection.

The flow of the first drug fluid B in the first drug line 16B is closed. This may be done by using a clamp 18B on the first drug line 16B. The flow of the first drug fluid B may also be closed by the valve 100 by setting the valve handle into a different position than the first drug position. A European drug line would normally be equipped with a clamp.

The flushing container 12A should be shut off by the clamp 18A located upstream the valve 100 on the main IV line 16A, if all infusion bags 12A to 12C are located at the same head pressure.

This is in line with the procedure used today.

Operation of the Valve

In the two systems 50 and 50' shown in FIG. 11A and FIG. 11B, the valve 100 will operate as follows:

The flushing fluid A will flow to the patient from the flushing container 12A when the handle 304 is positioned in a valve position allowing fluid through the valve 100 from the flushing inlet F to the outlet O. Such a position may be one of the drug fluids described above. Such a valve position my optionally also be a dedicated or "pure" flushing position (FIG. 8A-FIG. 8F). The clamp 18A arranged on the downstream part of the main IV line 16 will be open. If using the dedicated flushing position, the valve 100 will ensure that no drug fluids B or C will flow through the valve 100 to the outlet O.

A drug fluid B or C will flow when the handle 304 is located in an associated drug position and when the clamp 18A located downstream the valve 100 is opened, and the associated clamp 18B, 18C on the associated secondary line 16B, 16C is also opened.

The flushing fluid A will not flow through the valve 100 when a drug fluid, say drug fluid B, is flowing through the valve 100 to the outlet. In the U.S: system, the flushing fluid flow may be prevented due to a pressure difference. The flushing fluid flow may also be prevented by closing the main IV line 16A upstream the valve 100 using a clamp 18A (if any).

In the U.S. system 50, when a drug IV set (16B, 16C) runs empty during drug administering, the flushing fluid A will automatically start flushing the main IV line 16A including the valve 100. It will be noted that this is a specific advantage of the valve, since the valve in each selected drug position also provides fluid connection to the flushing fluid. For the European system 50', the clamp 18A on the main IV line 16A needs to be opened before flushing is initiated.

Figure 15A:
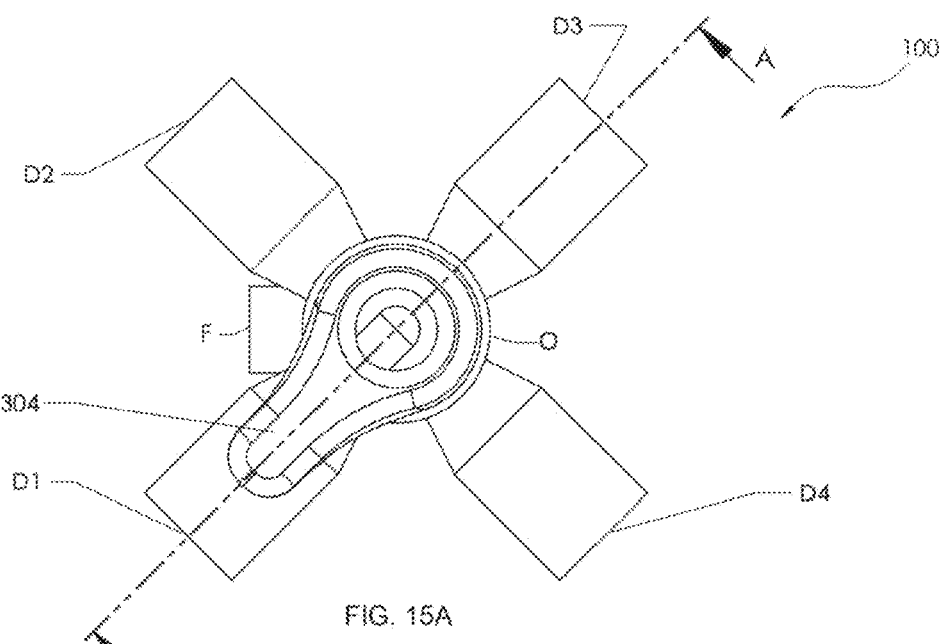
FIG. 15A illustrates an alternative embodiment of a valve with an alternative design of a distribution channel and provided with a bifurcation structure, shown in plan view.
Figure 15B:
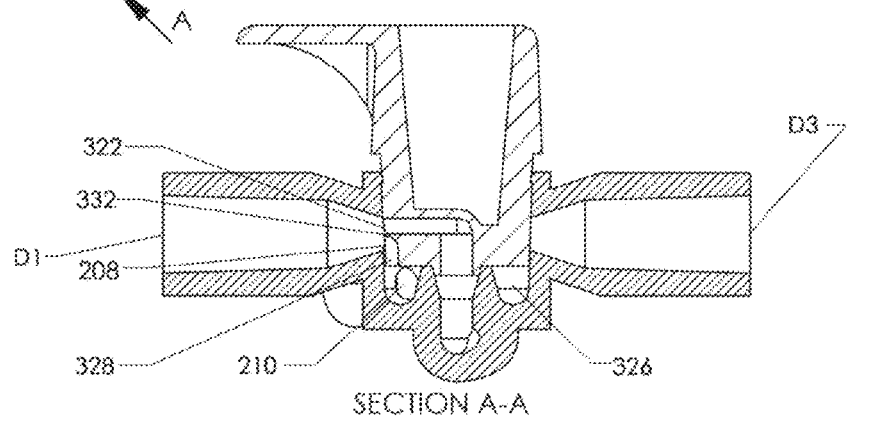
FIG. 15B illustrates a sectional view of the valve of FIG. 15A, in a section taken substantially along the line A-A in FIG. 15A.
Figure 15C:
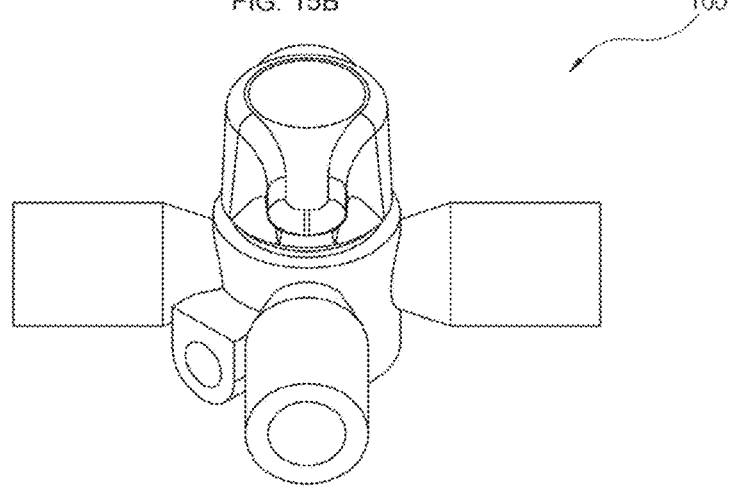
FIG. 15C illustrates a perspective view of the valve of FIG. 15A.

FIG. 15A-FIG. 15C illustrates an alternative embodiment of a valve, where the transfer channel 328 and main channel inlet 322 bifurcates the drug outlet 208 with a wall portion 332.

Figure 16A:
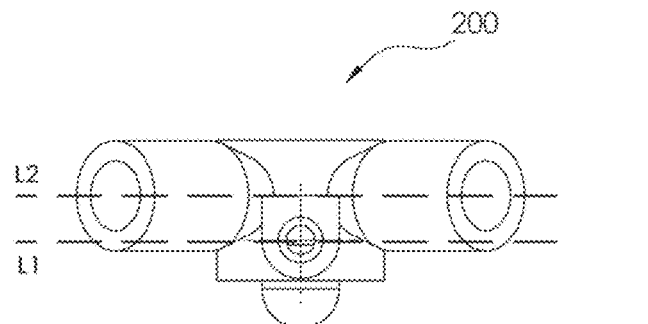
FIG. 16A illustrates a housing comprised in the valve in FIG. 15A, shown in elevational view.
Figure 16B:
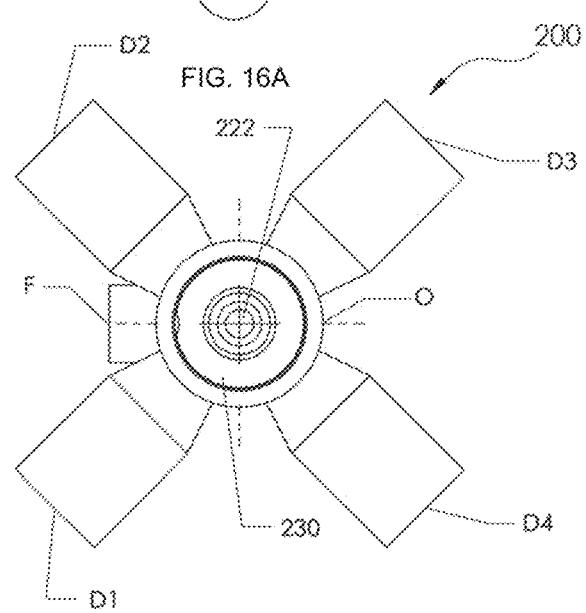
FIG. 16B illustrates the housing of FIG. 16A, shown in plan view.
Figure 16C:
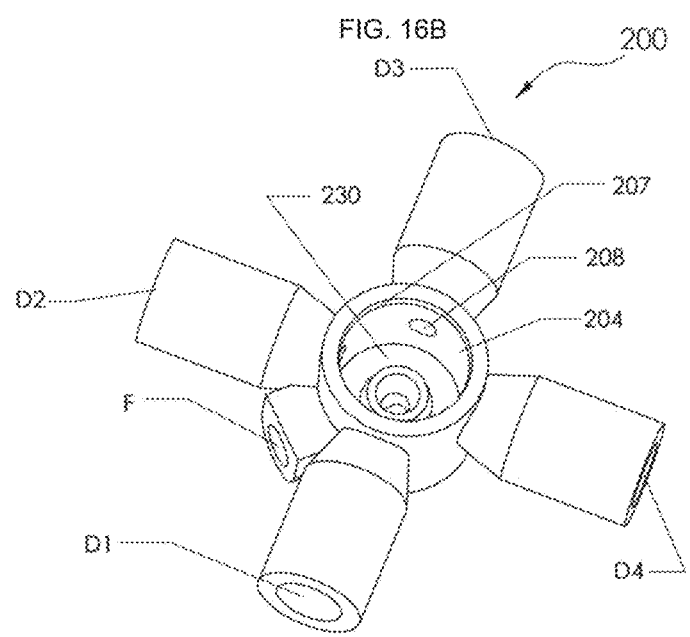
FIG. 16C illustrates the housing of FIG. 16A, shown in perspective view.

FIG. 16A-FIG. 16C illustrates a housing comprised in the valve in FIG. 15A-FIG. 15C with a closed bottom 230 that forms a part of the distribution channel 326

Figure 17A:
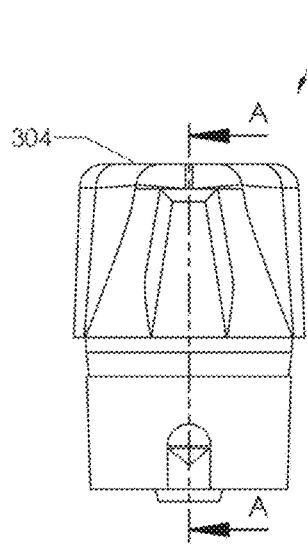
FIG. 17A illustrates a valve member comprised in the valve in FIG. 15A, shown in elevational view.
Figure 17B:
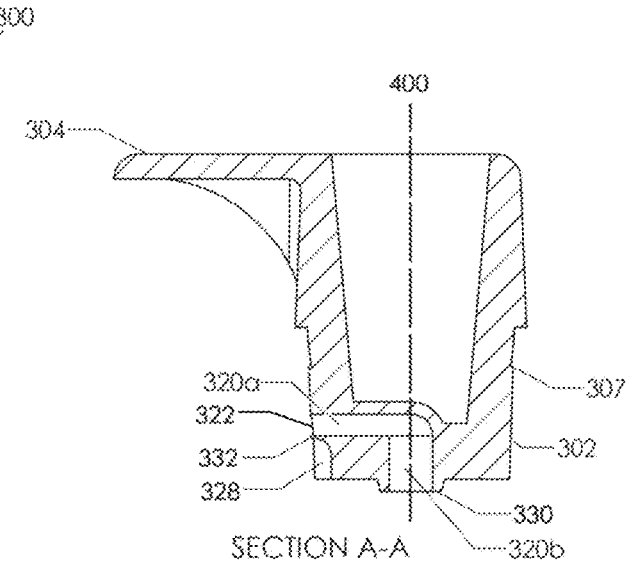
FIG. 17B illustrates the valve member of FIG. 17A, shown in a sectional view taken substantially along the line A-A in FIG. 17A.
Figure 17C:
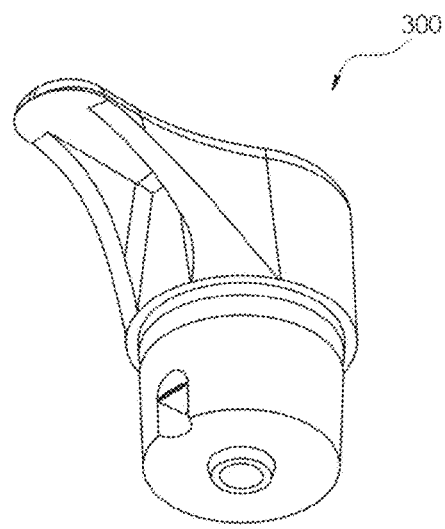
FIG. 17C illustrates the valve member of FIG. 17A, shown in perspective view.

FIG. 17A-FIG. 17C illustrates a valve member compromised in the valve FIG. 15A-FIG. 15C with a transfer channel 328 and main channel 322 and a wall section 332.

FIG. 18A-FIG. 18F illustrates an alternative embodiment including a back check valve 500 integrated in the transfer channel 328. The back check valve 500 as shown in FIG. 18C-FIG. 18D, and FIG. 18F is a small lip fitted into a recess 333 in the valve member 300 and it may be glued in place and or be press fitted. The lip and the recess in the valve member may be constructed such that the lip can deflect in one direction but not in the other direction, in order to allow fluid to flow downstream but not upstream in the transfer channel. The lip may be constructed of a silicon or rubber material.

I claim:

1. A valve for administering two or more drug fluids, comprising:
   a rotational axis,
   a housing having:
      an inner cavity
      an inner circumferential surface,
      one flushing inlet for receiving a flushing fluid, the flushing inlet being fluidly connected to a flushing outlet, which opens into the inner cavity and is positioned on a first level with respect to the rotational axis, and
      a plurality of drug inlets, each drug inlet for receiving an associated drug fluid and each drug inlet being fluidly connected to an associated drug outlet opening into the inner cavity and being positioned on a second level that is different from the first level; and
   a rotatable valve member having:
      an outer circumferential surface, a main passageway presenting an inlet arranged in the outer circumferential surface at the second level and an outlet arranged coaxially with the rotational axis; and a transfer channel formed at an interface between the housing and the rotatable valve member, said transfer channel being located between said first and said second level for carrying the flushing fluid;

wherein the rotatable valve member is arranged to be rotated into any selected one of a plurality of drug positions, each drug position being associated with a respective one of said drug outlets; and wherein, in each selected drug position, the drug outlet which is associated with the selected drug position is fluidly connected, simultaneously, to both the inlet of the main passageway and to the flushing outlet via the transfer channel of the rotatable member.

2. The valve according to claim 1, further comprising a distribution channel for carrying the flushing fluid, and formed at an interface between the housing and the valve member, said distribution channel being circumferentially oriented in relation to the rotational axis and fluidly connected to the flushing outlet;

wherein, the transfer channel of the rotatable valve member is fluidly connected to the distribution channel and extends at least partly in the direction of the rotational axis towards the second level.

3. The valve according to claim 2, wherein the transfer channel of the rotatable valve member is directly connected within the valve member to the main passageway.

4. The valve according to claim 2, wherein the housing further comprises a plurality of flushing recesses formed in the inner circumferential surface of the valve housing, each flushing recess being associated with a selected drug position and extending at least partly in the direction of the rotational axis and being fluidly connected to an associated drug outlet; and wherein, in each selected drug position, the drug outlet which is associated with the selected drug position is fluidly connected to the flushing outlet via a flow path formed by the distribution channel, the transfer channel and a flushing recess which is associated with the selected drug position.

5. The valve according to claim 2, wherein the transfer channel has a first end, which is located on the first level and is fluidly connected to the distribution channel, and a second end, which is located adjacent to the second level and which together with the inlet of the main passageway, in each selected drug position, bifurcates a drug outlet associated with the selected drug position.

6. The valve according to claim 2, wherein the distribution channel extends in a circumferential direction over 360 degrees to form a complete annular distribution channel.

7. The valve according to claim 2, wherein the distribution channel extends in a circumferential direction less than 360 degrees to form a partial annular distribution channel.

8. The valve according to claim 1, wherein the valve member is further arranged to be positioned into any selected one of one or more flushing positions; and wherein, in each selected flushing position, the inlet of the main passageway is fluidly connected to the flushing outlet via the transfer channel of the rotatable valve member but not to any one of the drug outlets.

9. The valve according to claim 1, wherein the inner circumferential surface of the housing is in sealing engagement with the outer circumferential surface of the valve member.

10. The valve according to claim 1, wherein the inner circumferential surface of the housing and the outer circumferential surface of the valve member are cylindrical.

11. The valve according to claim 1, wherein the inner circumferential surface of the housing and the outer circumferential surface of the valve member are conical or frustoconical.

12. The valve according to claim 1, wherein the main passageway comprises a first part extending from the inlet of the main passageway towards the rotational axis, and a second part extending coaxially with the rotational axis, from a radially inner end of the first part of the main passageway, towards the outlet of the main passageway.

13. The valve according to claim 1, wherein the plurality of drug positions constitute the only rotary positions of the valve member allowing a drug to be administered from a drug inlet to an outlet of the valve.

14. The valve according to claim 1, wherein the valve member is provided with a handle for rotating the valve member and wherein the first level is located closer to the handle than the second level.

15. The valve according to claim 1, wherein the valve member is provided with a handle for rotating the valve member and wherein the second level is located closer to the handle than the first level.

16. The valve according to claim 1, wherein the valve member is provided with a handle for rotating the valve member, wherein in each selected drug position the handle is aligned with a drug inlet associated with the selected drug position.

17. A valve for administering two or more drug fluids comprising:

an outlet,
a rotational axis,
a housing having:
an inner cavity
an inner circumferential surface,
one flushing inlet for receiving a flushing fluid, the flushing inlet being fluidly connected to a flushing outlet of the housing, which opens into the inner cavity and is positioned on a first level with respect to the rotational axis, and
a plurality of drug inlets, each drug inlet for receiving an associated drug fluid and each drug inlet being fluidly connected to an associated drug outlet opening of the housing into the inner cavity and being positioned on a second level that is different from the first level; and a rotatable valve member having:
an outer circumferential surface,
a main passageway presenting an inlet arranged in the outer circumferential surface at the second level and an outlet arranged coaxially with the rotational axis; and
a transfer channel formed at an interface between the housing and the rotatable valve member, said transfer channel being located between said first and said second level for carrying the flushing fluid;

wherein the valve member is arranged to be rotated into any selected one of a plurality of drug positions, each drug position being associated with a respective one of said drug outlets; and wherein the valve presents simultaneously, in each selected drug position:
- a drug flow path extending from the associated drug outlet, through the main passageway, and to the outlet of the valve,
- a flushing flow path extending from the flushing outlet to the outlet of the valve and comprising a first part, including the transfer channel, not being common with the drug flow path and a second part, including the main passage way, being common with the drug flow path, and
- a backpriming flow path extending from the flushing outlet to the associated drug outlet and being at least partly common with the first part of the flushing flow path.

* * * * *